US012751858B2

(12) United States Patent
Karnik et al.

(10) Patent No.: US 12,751,858 B2
(45) Date of Patent: Oct. 6, 2026

(54) METHODS, SYSTEMS, AND DEVICES FOR TREATING NERVE SPASTICITY

(71) Applicant: Pacira CryoTech, Inc., Tampa, FL (US)

(72) Inventors: Jwala Karnik, Santa Barbara, CA (US); John Allison, Los Altos, CA (US); Clint Carnell, Park City, UT (US)

(73) Assignee: Pacira CryoTech, Inc., Tampa, FL (US)

( * ) Notice: Subject to any disclaimer, the term of this patent is extended or adjusted under 35 U.S.C. 154(b) by 31 days.

(21) Appl. No.: 18/519,876

(22) Filed: Nov. 27, 2023

(65) Prior Publication Data

US 2024/0091056 A1 Mar. 21, 2024

Related U.S. Application Data

(60) Continuation of application No. 17/571,307, filed on Jan. 7, 2022, now Pat. No. 11,865,038, which is a (Continued)

(51) Int. Cl.

*A61B 18/02* (2006.01)
*A61F 7/12* (2006.01)

(Continued)

(52) U.S. Cl.

CPC ................ *A61F 7/12* (2013.01); *A61B 18/02* (2013.01); *A61M 5/00* (2013.01); *A61N 1/403* (2013.01);

(Continued)

(58) Field of Classification Search

CPC ................ A61B 18/02; A61B 18/0218; A61B 2018/0262; A61B 2018/00041;

(Continued)

(56) References Cited

U.S. PATENT DOCUMENTS 2,319,542 A 5/1943 Hall
2,672,032 A 3/1954 Towse (Continued)

FOREIGN PATENT DOCUMENTS

CA 2643474 9/2007
CN 105208954 A 12/2015

(Continued)

OTHER PUBLICATIONS

U.S. Appl. No. 61/116,050, Cryosurgical Safety Valve Arrangement and Methods for Its Use in Cosmetic and Other Treatment, filed Nov. 19, 2008, 35 pages.

(Continued)

*Primary Examiner* — Thomas A Giuliani

(74) *Attorney, Agent, or Firm* — Kilpatrick Townsend & Stockton LLP

(57) ABSTRACT

A method in which a nerve associated with a spasticity in a limb of a patient may be identified. The cryogenic cooling needle may be inserted through a skin surface. The cryogenic cooling needle may be positioned to a target tissue such that the distal end of the cryogenic cooling needle is proximate to the nerve by bending the needle, wherein the needle has varying stiffness at a proximal portion and a distal portion. A treatment cycle may be delivered to a target tissue proximate to the nerve, the treatment cycle may comprise a cooling phase wherein cooling fluid flows into the lumen so that liquid from the cooling fluid flow vaporizes within the lumen to provide cooling to the nerve so as to treat spasticity.

19 Claims, 20 Drawing Sheets

Related U.S. Application Data continuation of application No. 16/132,205, filed on Sep. 14, 2018, now Pat. No. 11,253,393, which is a division of application No. 14/218,146, filed on Mar. 18, 2014, now Pat. No. 10,085,881.

(60) Provisional application No. 61/801,268, filed on Mar. 15, 2013, provisional application No. 61/800,478, filed on Mar. 15, 2013.

(51) Int. Cl.

| | |
|---|---|
| ***A61M 5/00*** | (2006.01) |
| ***A61N 1/40*** | (2006.01) |
| *A61B 18/00* | (2006.01) |
| *A61B 18/14* | (2006.01) |
| *A61F 7/00* | (2006.01) |
| *A61F 7/02* | (2006.01) |

(52) U.S. Cl.
CPC ............... *A61B 2018/00041* (2013.01); *A61B 2018/00434* (2013.01); *A61B 2018/0293* (2013.01); *A61B 2018/1425* (2013.01); *A61F 2007/0042* (2013.01); *A61F 2007/0087* (2013.01); *A61F 2007/0285* (2013.01); *A61M 2202/0484* (2013.01); *A61M 2210/086* (2013.01)

(58) Field of Classification Search
CPC .... A61B 2018/00434; A61B 2018/025; A61B 2018/0293; A61B 2018/00005; A61B 2018/00011; A61B 2018/00029; A61B 2018/00452; A61B 2018/00458; A61B 2018/00464; A61B 2018/0047; A61B 2018/00476; A61N 1/403; A61F 7/12; A61F 2007/0087; A61F 2007/0285
USPC ....... 606/20–26; 607/96, 104, 105, 113, 114
See application file for complete search history.

(56) References Cited

U.S. PATENT DOCUMENTS

| | | | |
|---|---|---|---|
| 2,922,420 | A | 1/1960 | Cheng |
| 3,226,492 | A | 12/1965 | Schuetze |
| 3,266,492 | A | 8/1966 | Steinberg |
| 3,289,424 | A | 12/1966 | Shepherd |
| 3,343,544 | A | 9/1967 | Dunn et al. |
| 3,351,063 | A | 11/1967 | Malaker et al. |
| 3,439,680 | A | 4/1969 | Thomas, Jr. |
| 3,483,869 | A | 12/1969 | Hayhurst |
| 3,502,081 | A | 3/1970 | Amoils |
| 3,507,283 | A | 4/1970 | Thomas, Jr. |
| 3,532,094 | A | 10/1970 | Stahl |
| 3,664,344 | A | 5/1972 | Bryne |
| 3,702,114 | A | 11/1972 | Zacarian |
| 3,795,245 | A | 3/1974 | Allen, Jr. et al. |
| 3,814,095 | A | 6/1974 | Lubens |
| 3,830,239 | A | 8/1974 | Stumpf et al. |
| 3,886,945 | A | 6/1975 | Stumpf et al. |
| 3,889,681 | A | 6/1975 | Waller et al. |
| 3,910,278 | A | 10/1975 | Crandell et al. |
| 3,951,152 | A | 4/1976 | Crandell et al. |
| 3,993,075 | A | 11/1976 | Lisenbee et al. |
| 4,140,109 | A | 2/1979 | Savic et al. |
| 4,207,897 | A | 6/1980 | Lloyd et al. |
| 4,236,518 | A | 12/1980 | Floyd |
| 4,306,568 | A | 12/1981 | Torre |
| 4,376,376 | A | 3/1983 | Gregory |
| 4,404,862 | A | 9/1983 | Harris, Sr. |
| 4,524,771 | A | 6/1985 | McGregor et al. |
| 4,758,217 | A | 7/1988 | Gueret |
| 4,802,475 | A | 2/1989 | Weshahy |
| 4,945,434 | A | 7/1990 | Wilmer et al. |
| 4,946,460 | A | 8/1990 | Merry et al. |
| 5,059,197 | A | 10/1991 | Urie et al. |
| 5,200,170 | A | 4/1993 | McDow |
| 5,201,729 | A | 4/1993 | Hertzmann et al. |
| 5,294,325 | A | 3/1994 | Liu |
| 5,334,181 | A | 8/1994 | Rubinsky et al. |
| 5,417,689 | A | 5/1995 | Fine |
| 5,520,681 | A | 5/1996 | Fuller et al. |
| 5,571,147 | A | 11/1996 | Sluijter et al. |
| 5,647,868 | A | 7/1997 | Chinn |
| 5,747,777 | A | 5/1998 | Matsuoka |
| 5,755,753 | A | 5/1998 | Knowlton |
| 5,759,182 | A | 6/1998 | Varney et al. |
| 5,814,040 | A | 9/1998 | Nelson et al. |
| 5,860,970 | A | 1/1999 | Goddard et al. |
| 5,879,378 | A | 3/1999 | Usui |
| 5,899,897 | A | 5/1999 | Rabin et al. |
| 5,916,212 | A | 6/1999 | Baust et al. |
| 5,971,983 | A | 10/1999 | Lesh |
| 5,976,505 | A | 11/1999 | Henderson |
| 6,003,539 | A | 12/1999 | Yoshihara |
| 6,032,675 | A | 3/2000 | Rubinsky |
| 6,039,730 | A | 3/2000 | Rabin et al. |
| 6,041,787 | A | 3/2000 | Rubinsky |
| 6,139,545 | A | 10/2000 | Utley et al. |
| 6,141,985 | A | 11/2000 | Cluzeau et al. |
| 6,142,991 | A | 11/2000 | Schatzberger |
| 6,162,202 | A | 12/2000 | Sicurelli et al. |
| 6,182,666 | B1 | 2/2001 | Dobak, III |
| 6,193,672 | B1 | 2/2001 | Clement |
| 6,196,839 | B1 | 3/2001 | Ross |
| 6,238,386 | B1 | 5/2001 | Muller et al. |
| 6,272,384 | B1 | 8/2001 | Simon et al. |
| 6,277,099 | B1 | 8/2001 | Strowe et al. |
| 6,277,116 | B1 | 8/2001 | Utely et al. |
| 6,363,730 | B1 | 4/2002 | Thomas et al. |
| 6,364,899 | B1 | 4/2002 | Dobak, III |
| 6,371,943 | B1 | 4/2002 | Racz et al. |
| 6,432,102 | B2 | 8/2002 | Joye et al. |
| 6,494,844 | B1 | 12/2002 | Van Bladel et al. |
| 6,503,246 | B1 | 1/2003 | Har-Shai et al. |
| 6,506,796 | B1 | 1/2003 | Fesus et al. |
| 6,512,958 | B1 | 1/2003 | Swoyer et al. |
| 6,546,935 | B2 | 4/2003 | Hooven |
| 6,547,769 | B2 | 4/2003 | VanTassel et al. |
| 6,551,309 | B1 | 4/2003 | LePivert |
| 6,562,021 | B1 | 5/2003 | Derbin et al. |
| 6,562,030 | B1 | 5/2003 | Abboud et al. |
| 6,564,079 | B1 | 5/2003 | Cory et al. |
| 6,629,951 | B2 | 10/2003 | Laufer et al. |
| 6,648,880 | B2 | 11/2003 | Chauvet et al. |
| 6,669,688 | B2 | 12/2003 | Svaasand et al. |
| 6,672,095 | B1 | 1/2004 | Luo |
| 6,682,501 | B1 | 1/2004 | Nelson et al. |
| 6,706,037 | B2 | 3/2004 | Zvuloni et al. |
| 6,723,092 | B2 | 4/2004 | Brown et al. |
| 6,749,624 | B2 | 6/2004 | Knowlton |
| 6,761,715 | B2 | 7/2004 | Carroll |
| 6,764,493 | B1 | 7/2004 | Weber et al. |
| 6,786,901 | B2 | 9/2004 | Joye et al. |
| 6,786,902 | B1 | 9/2004 | Rabin et al. |
| 6,789,545 | B2 | 9/2004 | Littrup et al. |
| 6,840,935 | B2 | 1/2005 | Lee |
| 6,858,025 | B2 | 2/2005 | Maurice |
| 6,896,666 | B2 | 5/2005 | Kochamba |
| 6,902,554 | B2 | 6/2005 | Huttner |
| 6,905,492 | B2 | 6/2005 | Zvuloni et al. |
| 6,905,494 | B2 | 6/2005 | Yon et al. |
| 6,936,048 | B2 | 8/2005 | Hurst |
| 6,944,490 | B1 | 9/2005 | Chow |
| 6,960,208 | B2 | 11/2005 | Bourne et al. |
| 7,001,400 | B1 | 2/2006 | Modesitt et al. |
| 7,081,111 | B2 | 7/2006 | Svaasand et al. |
| 7,081,112 | B2 | 7/2006 | Joye et al. |
| 7,083,612 | B2 | 8/2006 | Littrup et al. |
| 7,189,230 | B2 | 3/2007 | Knowlton |
| 7,195,616 | B2 | 3/2007 | Diller et al. |
| 7,207,985 | B2 | 4/2007 | Duong et al. |
| 7,217,939 | B2 | 5/2007 | Johansson et al. |

(56) References Cited

U.S. PATENT DOCUMENTS

| | | | | |
|---|---|---|---|---|
| 7,250,046 | B1 | 7/2007 | Fallat | |
| 7,278,991 | B2 | 10/2007 | Morris et al. | |
| 7,311,672 | B2 | 12/2007 | Van Bladel et al. | |
| 7,322,973 | B2 | 1/2008 | Nahon | |
| 7,338,504 | B2 | 3/2008 | Gibbens, III et al. | |
| 7,347,840 | B2 | 3/2008 | Findlay et al. | |
| 7,367,341 | B2 | 5/2008 | Anderson et al. | |
| 7,402,140 | B2 | 7/2008 | Spero et al. | |
| 7,422,586 | B2 | 9/2008 | Morris et al. | |
| 7,479,139 | B2 | 1/2009 | Cytron et al. | |
| 7,507,234 | B2 | 3/2009 | Utley et al. | |
| 7,549,424 | B2 | 6/2009 | Desai | |
| 7,578,819 | B2 | 8/2009 | Bleich et al. | |
| 7,641,679 | B2 | 1/2010 | Joye et al. | |
| 7,653,438 | B2 | 1/2010 | Deem et al. | |
| 7,713,266 | B2 | 5/2010 | Elkins et al. | |
| 7,842,047 | B2 | 11/2010 | Modesitt et al. | |
| 7,846,170 | B2 | 12/2010 | Modesitt et al. | |
| 7,850,683 | B2 | 12/2010 | Elkins et al. | |
| 7,862,558 | B2 | 1/2011 | Elkins et al. | |
| 7,998,137 | B2 | 8/2011 | Elkins et al. | |
| 8,027,718 | B2 | 9/2011 | Spinner et al. | |
| 8,038,688 | B2 | 10/2011 | Modesitt et al. | |
| 8,298,216 | B2 | 10/2012 | Burger et al. | |
| 8,409,185 | B2 | 4/2013 | Burger et al. | |
| 8,461,108 | B2 | 6/2013 | Hsu et al. | |
| 8,617,228 | B2 | 12/2013 | Wittenberger et al. | |
| 8,715,275 | B2 | 5/2014 | Burger et al. | |
| 8,722,065 | B2 | 5/2014 | Ishibashi et al. | |
| 9,017,318 | B2 | 4/2015 | Fourkas et al. | |
| 9,039,688 | B2 | 5/2015 | Palmer, III et al. | |
| 9,066,712 | B2 | 6/2015 | Fourkas et al. | |
| 9,072,498 | B2 | 7/2015 | Elkins et al. | |
| 9,101,346 | B2 | 8/2015 | Burger et al. | |
| 9,155,584 | B2 | 10/2015 | Fourkas et al. | |
| 9,241,753 | B2 | 1/2016 | Fourkas et al. | |
| 9,254,162 | B2 | 2/2016 | Burger et al. | |
| 9,295,512 | B2 | 3/2016 | Allison et al. | |
| 9,314,290 | B2 | 4/2016 | Fourkas et al. | |
| 9,610,112 | B2 | 4/2017 | Karnik et al. | |
| 9,668,800 | B2 | 6/2017 | Karnik et al. | |
| 9,907,693 | B2 | 3/2018 | Burger et al. | |
| 10,016,229 | B2 | 7/2018 | Carnell et al. | |
| 10,085,789 | B2 | 10/2018 | Carnell et al. | |
| 10,085,881 | B2 | 10/2018 | Karnik et al. | |
| 10,314,739 | B2 | 6/2019 | Allison et al. | |
| 10,363,080 | B2 | 7/2019 | Elkins et al. | |
| 10,596,030 | B2 | 3/2020 | Karnik et al. | |
| 10,888,366 | B2 | 1/2021 | Allison | |
| 11,134,999 | B2 | 10/2021 | Carnell et al. | |
| 11,253,393 | B2 * | 2/2022 | Karnik .................... | A61M 5/00 |
| 11,642,241 | B2 * | 5/2023 | Karnik .................... | A61B 18/02 607/105 |
| 11,865,038 | B2 | 1/2024 | Karnik et al. | |
| 2002/0010460 | A1 | 1/2002 | Joye et al. | |
| 2002/0013602 | A1 | 1/2002 | Huttner | |
| 2002/0045434 | A1 | 4/2002 | Masoian et al. | |
| 2002/0049436 | A1 | 4/2002 | Zvuloni et al. | |
| 2002/0068929 | A1 | 6/2002 | Zvuloni | |
| 2002/0087152 | A1 | 7/2002 | Mikus et al. | |
| 2002/0087208 | A1 | 7/2002 | Koblish et al. | |
| 2002/0095144 | A1 | 7/2002 | Carl | |
| 2002/0120260 | A1 | 8/2002 | Morris et al. | |
| 2002/0120261 | A1 | 8/2002 | Morris et al. | |
| 2002/0120263 | A1 | 8/2002 | Brown et al. | |
| 2002/0128638 | A1 | 9/2002 | Chauvet et al. | |
| 2002/0156469 | A1 | 10/2002 | Yon et al. | |
| 2002/0183731 | A1 | 12/2002 | Holland et al. | |
| 2002/0193778 | A1 | 12/2002 | Alchas et al. | |
| 2003/0036752 | A1 | 2/2003 | Joye et al. | |
| 2003/0109912 | A1 | 6/2003 | Joye et al. | |
| 2003/0130575 | A1 | 7/2003 | Desai | |
| 2003/0144709 | A1 | 7/2003 | Zabara et al. | |
| 2003/0171742 | A1 | 9/2003 | Mihalik et al. | |
| 2003/0181896 | A1 | 9/2003 | Zvuloni et al. | |
| 2003/0195436 | A1 | 10/2003 | Van Bladel et al. | |
| 2003/0220635 | A1 | 11/2003 | Knowlton et al. | |
| 2003/0220674 | A1 | 11/2003 | Anderson et al. | |
| 2004/0024391 | A1 | 2/2004 | Cytron et al. | |
| 2004/0082943 | A1 | 4/2004 | Littrup et al. | |
| 2004/0092875 | A1 | 5/2004 | Kochamba | |
| 2004/0122482 | A1 | 6/2004 | Tung et al. | |
| 2004/0143252 | A1 | 7/2004 | Hurst | |
| 2004/0162551 | A1 | 8/2004 | Brown et al. | |
| 2004/0167505 | A1 | 8/2004 | Joye et al. | |
| 2004/0191229 | A1 | 9/2004 | Link, Jr. et al. | |
| 2004/0204705 | A1 | 10/2004 | Lafontaine | |
| 2004/0210212 | A1 * | 10/2004 | Maurice ............. | A61B 18/1477 606/23 |
| 2004/0215178 | A1 | 10/2004 | Maurice | |
| 2004/0215294 | A1 | 10/2004 | Littrup et al. | |
| 2004/0215295 | A1 | 10/2004 | Littrup et al. | |
| 2004/0220497 | A1 | 11/2004 | Findlay et al. | |
| 2004/0220648 | A1 | 11/2004 | Carroll | |
| 2004/0225276 | A1 | 11/2004 | Burgess | |
| 2004/0231683 | A1 | 11/2004 | Eng et al. | |
| 2004/0243116 | A1 | 12/2004 | Joye et al. | |
| 2004/0267248 | A1 | 12/2004 | Duong et al. | |
| 2004/0267257 | A1 | 12/2004 | Bourne et al. | |
| 2005/0004563 | A1 | 1/2005 | Racz et al. | |
| 2005/0027334 | A1 | 2/2005 | Lentz et al. | |
| 2005/0059964 | A1 | 3/2005 | Fitz | |
| 2005/0065504 | A1 | 3/2005 | Melsky et al. | |
| 2005/0131508 | A1 | 6/2005 | Garabedian et al. | |
| 2005/0177147 | A1 | 8/2005 | Vancelette et al. | |
| 2005/0177148 | A1 | 8/2005 | van der Walt et al. | |
| 2005/0182394 | A1 | 8/2005 | Spero et al. | |
| 2005/0203505 | A1 | 9/2005 | Megerman et al. | |
| 2005/0203593 | A1 | 9/2005 | Shanks et al. | |
| 2005/0209565 | A1 | 9/2005 | Yuzhakov et al. | |
| 2005/0209587 | A1 | 9/2005 | Joye et al. | |
| 2005/0222558 | A1 | 10/2005 | Baxter et al. | |
| 2005/0224086 | A1 | 10/2005 | Nahon | |
| 2005/0228288 | A1 | 10/2005 | Hurst | |
| 2005/0240171 | A1 | 10/2005 | Forrest | |
| 2005/0251103 | A1 | 11/2005 | Steffen et al. | |
| 2005/0261753 | A1 | 11/2005 | Littrup et al. | |
| 2005/0276759 | A1 | 12/2005 | Roser et al. | |
| 2005/0281530 | A1 | 12/2005 | Rizoiu et al. | |
| 2005/0283125 | A1 | 12/2005 | Barkhahn et al. | |
| 2005/0283148 | A1 | 12/2005 | Janssen et al. | |
| 2006/0009712 | A1 | 1/2006 | Van Bladel et al. | |
| 2006/0015092 | A1 | 1/2006 | Joye et al. | |
| 2006/0030845 | A1 | 2/2006 | Leung et al. | |
| 2006/0069385 | A1 | 3/2006 | Lafontaine et al. | |
| 2006/0079914 | A1 | 4/2006 | Modesitt et al. | |
| 2006/0084962 | A1 | 4/2006 | Joye et al. | |
| 2006/0089688 | A1 | 4/2006 | Panescu | |
| 2006/0095059 | A1 | 5/2006 | Bleich et al. | |
| 2006/0111732 | A1 | 5/2006 | Gibbens et al. | |
| 2006/0129142 | A1 | 6/2006 | Reynolds | |
| 2006/0142785 | A1 | 6/2006 | Modesitt et al. | |
| 2006/0173469 | A1 | 8/2006 | Klein et al. | |
| 2006/0189968 | A1 | 8/2006 | Howlett et al. | |
| 2006/0190035 | A1 | 8/2006 | Hushka et al. | |
| 2006/0200117 | A1 | 9/2006 | Hermans | |
| 2006/0212028 | A1 | 9/2006 | Joye et al. | |
| 2006/0212048 | A1 | 9/2006 | Crainich | |
| 2006/0223052 | A1 | 10/2006 | MacDonald et al. | |
| 2006/0224149 | A1 | 10/2006 | Hillely | |
| 2006/0258951 | A1 | 11/2006 | Bleich et al. | |
| 2007/0049924 | A1 | 3/2007 | Rahn | |
| 2007/0055173 | A1 | 3/2007 | Delonzor et al. | |
| 2007/0060921 | A1 | 3/2007 | Janssen et al. | |
| 2007/0088217 | A1 | 4/2007 | Babaev | |
| 2007/0088247 | A1 * | 4/2007 | Bliweis .............. | A61B 1/00154 606/21 |
| 2007/0129714 | A1 | 6/2007 | Elkins et al. | |
| 2007/0156125 | A1 | 7/2007 | DeLonzor | |
| 2007/0161975 | A1 | 7/2007 | Goulko | |
| 2007/0167943 | A1 | 7/2007 | Janssen et al. | |
| 2007/0167959 | A1 | 7/2007 | Modesitt et al. | |
| 2007/0179340 | A1 | 8/2007 | Jorgensen | |
| 2007/0179509 | A1 | 8/2007 | Nagata et al. | |

(56) References Cited

U.S. PATENT DOCUMENTS

2007/0198071 A1 8/2007 Ting et al.
2007/0225781 A1 9/2007 Saadat et al.
2007/0255362 A1 11/2007 Levinson et al.
2007/0270925 A1 11/2007 Levinson
2008/0033415 A1 2/2008 Rieker et al.
2008/0051775 A1 2/2008 Evans
2008/0051776 A1 2/2008 Bliweis et al.
2008/0077201 A1 3/2008 Levinson et al.
2008/0077202 A1 3/2008 Levinson
2008/0077211 A1 3/2008 Levinson et al.
2008/0154254 A1 6/2008 Burger et al.
2008/0183164 A1* 7/2008 Elkins .................... A61B 18/02 606/21
2008/0200910 A1 8/2008 Burger et al.
2008/0287839 A1 11/2008 Rosen et al.
2009/0018623 A1 1/2009 Levinson et al.
2009/0018624 A1 1/2009 Levinson et al.
2009/0018625 A1 1/2009 Levinson et al.
2009/0018626 A1 1/2009 Levinson et al.
2009/0018627 A1 1/2009 Levinson et al.
2009/0036823 A1 2/2009 Lepivert
2009/0118722 A1 5/2009 Ebbers et al.
2009/0171334 A1 7/2009 Elkins et al.
2009/0248001 A1 10/2009 Burger et al.
2009/0264876 A1 10/2009 Roy et al.
2009/0299357 A1 12/2009 Zhou
2010/0016847 A1 1/2010 Fischer et al.
2010/0081971 A1 4/2010 Allison
2010/0114191 A1 5/2010 Newman
2010/0168725 A1 7/2010 Babkin et al.
2010/0241114 A1 9/2010 Privitera et al.
2010/0286691 A1 11/2010 Kerr et al.
2010/0305439 A1 12/2010 Shai et al.
2010/0331883 A1 12/2010 Schmitz et al.
2011/0087212 A1* 4/2011 Aldridge ............ A61B 18/1233 606/34
2011/0144631 A1 6/2011 Elkins et al.
2011/0178514 A1 7/2011 Levin et al.
2011/0196267 A1 8/2011 Mishelevich
2012/0065629 A1 3/2012 Elkins et al.
2012/0089211 A1 4/2012 Curtis et al.
2012/0165715 A1 6/2012 Murphy et al.
2012/0259322 A1 10/2012 Fourkas et al.
2012/0265187 A1 10/2012 Palmer, III et al.
2012/0277763 A1 11/2012 Greenblatt et al.
2013/0184694 A1* 7/2013 Fourkas ................. A61B 18/02 606/20
2013/0184695 A1 7/2013 Fourkas et al.
2013/0184696 A1 7/2013 Fourkas et al.
2013/0190745 A1* 7/2013 Fourkas ................. A61B 18/02 606/25
2013/0218148 A1 8/2013 Burger et al.
2013/0253605 A1 9/2013 Bennett et al.
2013/0261368 A1 10/2013 Schwartz
2013/0324990 A1 12/2013 Burger et al.
2014/0249519 A1 9/2014 Burger et al.
2014/0276539 A1 9/2014 Allison et al.
2014/0276708 A1 9/2014 Karnik et al.
2014/0343542 A1 11/2014 Karnik et al.
2014/0343543 A1 11/2014 Karnik et al.
2014/0343544 A1 11/2014 Carnell et al.
2014/0350536 A1 11/2014 Allison
2016/0095643 A1 4/2016 Fourkas et al.
2016/0166429 A1 6/2016 Allison et al.
2016/0183998 A1 6/2016 Fourkas et al.
2017/0239086 A1 8/2017 Karnik
2017/0258510 A1 9/2017 Carnell et al.
2019/0151006 A1 5/2019 Fourkas et al.
2020/0188005 A1 6/2020 Elkins et al.

FOREIGN PATENT DOCUMENTS

CN 105208954 B 6/2019
EP 0043447 1/1982
EP 0777123 A2 6/1997
EP 0955012 A1 11/1999
EP 1074273 2/2001
EP 1377327 1/2004
EP 1377327 B1 9/2007
EP 1862125 12/2007
EP 2499984 A1 9/2012
EP 2967706 A1 1/2016
EP 2967706 A4 12/2016
GB 1360353 A 7/1974
GB 1402632 8/1975
JP 60013111 A 1/1985
JP 04357945 A 12/1992
JP 0538347 A 2/1993
JP 10014656 A 1/1998
JP 2001178737 A 7/2001
JP 2004511274 A 4/2004
JP 2005080988 A 3/2005
JP 2006130055 A 5/2006
JP 2008515469 A 5/2008
RU 2254060 C2 6/2005
WO 9749344 A1 12/1997
WO 0197702 A1 12/2001
WO 0202026 A1 1/2002
WO 02092153 A2 11/2002
WO 2004039440 5/2004
WO 2004045434 A2 6/2004
WO 2004089460 10/2004
WO 2005000106 1/2005
WO 2005079321 9/2005
WO 2005096979 A1 10/2005
WO 2006012128 2/2006
WO 2006023348 A1 3/2006
WO 2006044727 A2 4/2006
WO 2006062788 A2 6/2006
WO 2006125835 A1 11/2006
WO 2006127467 A2 11/2006
WO 2007025106 A2 3/2007
WO 2007037326 A1 4/2007
WO 2007089603 8/2007
WO 2007109656 A2 9/2007
WO 2007129121 11/2007
WO 2007135629 11/2007
WO 2009026471 2/2009
WO 2010075438 A1 7/2010
WO 2010075448 A1 7/2010
WO 20141 46127 A1 9/2014
WO 2014146105 A2 9/2014
WO 2014146106 A2 9/2014
WO 2014146122 A1 9/2014
WO 2014146126 A1 9/2014
WO 2014146105 A3 11/2014
WO 2014146106 A3 12/2014

OTHER PUBLICATIONS

U.S. Appl. No. 61/800,478, Methods and Devices for Pain Management by John Allison et al., filed Mar. 15, 2013.

Bohannon et al., "Interrater Reliability of a Modified Ashworth Scale of Muscle Spasticity", Phys Ther., vol. 67, No. 2, Feb. 1987, pp. 206-207.

Boyd et al., "Objective Measurement of Clinical Findings in the Use of Botulinum Toxin Type A for the Management of Children with Cerebral Palsy", European Journal of Neurology, vol. 6, Supp. S4, 1999, pp. S23-S35.

Dasiou-Plakida , "Fat Injections for Facial Rejuvenation: 17 Years Experience in 1720 Patients", Journal of Cosmetic Dermatology, vol. 2, Nos. 3-4, Oct. 22, 2004, pp. 119-125.

Farrar et al., "Validity, Reliability, and Clinical Importance of Change in a 0-10 Numeric Rating Scale Measure of Spasticity: a Post HOC Analysis of a Randomized, Double-Blind, Placebo-Controlled Trial", Clin Ther., vol. 30, No. 5, 2008, pp. 974-985.

Foster et al., "Radiofrequency Ablation of Facial Nerve Branches Controlling Glabellar Frowning", Dermatologic Surgery, vol. 35, No. 12, Dec. 1, 2009, pp. 1908-1917.

Gallagher et al., "Prospective Validation of Clinically Important Changes in Pain Severity Measured on a Visual Analog Scale", Annals of Emergency Medicine, vol. 38, No. 6, 2001, pp. 633-638.

(56) References Cited

OTHER PUBLICATIONS

Har-Shai et al., "Effect of Skin Surface Temperature on Skin Pigmentation During Contact and Intralesional Cryosurgery of Hypertrophic Scars and Kleoids", Journal of the European Academy of Dermatology and Venereology, vol. 21, No. 2, Feb. 2007, pp. 1-14.
Magalov et al., "Isothermal Volume Contours Generated in a Freezing Gel by Embedded Cryo-Needles with Applications to Cryo-Surgery", Cryobiology, vol. 55, No. 2, Oct. 2007, pp. 127-137.
Morris , "Ashworth and Tardieu Scales: Their Clinical Relevance for Measuring Spasticity in Adult and Paediatric Neurological Populations", Physical Therapy Reviews, vol. 7, No. 1, 2002, pp. 53-62.
Page et al., "Clinically Important Differences for the Upper-Extremity Fugl-Meyer Scale in People with Minimal to Moderate Impairment Due to Chronic Stroke", Physical Therapy, vol. 92, No. 6, Jan. 26, 2012, pp. 791-798.
Penn et al., "Intrathecal Baclofen for Severe Spinal Spasticity", N Engl J Med., vol. 320, No. 23, Jun. 8, 1989, pp. 1517-1521.
Rewcastle et al., "A Model for the Time Dependent Three-Dimensional Thermal Distribution within Iceballs Surrounding Multiple Cryoprobes", Medical Physics, vol. 28, No. 6, Jun. 2001, pp. 1125-1137.
Rutkove , "Effects of Temperature on Neuromuscular Electrophysiology", Muscle & Nerve, vol. 24, No. 7, Jul. 2001, pp. 867-882.
Shaw et al., "BoTULS: A Multicentre Randomised Controlled Trial to Evaluate the Clinical Effectiveness and Cost-Effectiveness of Treating Upper Limb Spasticity Due to Stroke with Botulinum Toxin Type A", Health Technol Assess., vol. 14, No. 26, May 2010, 158 pages.
Sullivan et al., "Fugl-Meyer Assessment of Sensorimotor Function After Stroke: Standardized Training Procedure for Clinical Practice and Clinical Trials", Stroke, vol. 42, No. 2, Feb. 2011, pp. 427-432.
Utley et al., "Radiofrequency Ablation of the Nerve to the Corrugator Muscle for Elimination of Glabellar Furrowing", Archives of Facial Plastic Surgery, vol. 1, No. 1, Jan.-Mar. 1999, pp. 46-48.
Yang et al., "Apoptosis Induced by Cryo-Injury in Human Colorectal Cancer Cells is Associated with Mitochondrial Dysfunction", International Journal of Cancer, vol. 103, No. 3, Jan. 20, 2003, pp. 360-369.
U.S. Appl. No. 14/025,527, filed Sep. 12, 2013.
U.S. Appl. No. 14/218,146, filed Mar. 18, 2014.
U.S. Appl. No. 14/218,167, filed Mar. 18, 2014.
U.S. Appl. No. 14/218,925, filed Mar. 18, 2014.

* cited by examiner

Needle Hub Temperature Control Algorithm

METHODS, SYSTEMS, AND DEVICES FOR TREATING NERVE SPASTICITY

CROSS-REFERENCES TO RELATED APPLICATIONS

The present application is a Continuation of U.S. patent application Ser. No. 17/571,307 filed Jan. 7, 2022 (now U.S. Pat. No. 11,865,038), which is a continuation of U.S. patent application Ser. No. 16/132,205 filed Sep. 14, 2018 (now U.S. Pat. No. 11,253,393); which is a Divisional of U.S. patent application Ser. No. 14/218,146 filed Mar. 18, 2014 (now U.S. Pat. No. 10,085,881); which claims the benefit of U.S. Provisional Application Nos. 61/800,478 and 61/801,268, both of which were filed Mar. 15, 2013; the full disclosures which are incorporated herein by reference in their entirety for all purposes.

BACKGROUND OF THE INVENTION

The present invention is directed to medical devices, systems, and methods, particularly for those which employ cold for treatment of neuromas or fibromas associated with limb pain in a patient. Embodiments of the invention include cryogenic cooling needles that can be advanced through skin or other tissues to treat neuromas and fibromas, and/or to inhibit transmission of pain signals.

Over 100 million patients in the United States suffer from chronic pain. Chronic pain conditions are often debilitating, taking a toll on a patient's physical and mental welfare. Though a variety of pain management techniques currently exist, the most common nonsurgical options provide slow-acting and/or short-term relief. Medication, often in the form of non-steroidal anti-inflammatory drugs (NSAIDs) and opioids, comes with an array of side effects such as nausea and vomiting. Medication also presents the possibility of more serious effects such as increased risk of heart attack and stroke, and tolerance or dependency issues. Surgical strategies tend to be reserved for more severe cases and are limited by the risks and complications typically associated with surgery including bleeding, bruising, scarring, and infection.

A nonsurgical, minimally invasive, long-lasting approach to chronic pain management is desirable. In general, it would be advantageous to provide improved devices, systems, and methods for management of chronic and/or acute pain. Such improved techniques may avoid or decrease the systemic effects of toxin-based neurolysis and pharmaceutical approaches, while decreasing the invasiveness and/or collateral tissue damage of at least some known pain treatment techniques.

BRIEF SUMMARY OF THE INVENTION

Many embodiments provide a novel, minimally invasive device and method for providing focused cold therapy to target peripheral sensory nerve tissue that offers long-lasting pain relief through cryoanalgesia. The device and method may operate on the cryobiology principle that localized exposure to controlled moderately low temperature conditions can alter tissue function. The device and therapy may treat nerves with low temperatures via a cold probe in the form of an assembly of small diameter needles, creating a highly localized treatment zone around the probe. This focused cold therapy (FCT) may create a conduction block that prevents nerve signaling. Further, preliminary studies have provided preliminary evidence of the device and method effectiveness on motor nerves and have been shown to be safe with no serious device-related adverse events.

In some embodiments, a system for treating a neuroma or other painful condition (e.g., nerve entrapment, plantar fasciitis, fibromas, or the like) in a limb of a patient is provided. The system may include a needle having a proximal end, a distal end, and a needle lumen therebetween. The needle may be configured for insertion proximate to the nerve. A cooling fluid supply lumen may extend distally within the needle lumen to a distal portion of the needle lumen. A cooling fluid source may be couplable to the cooling fluid supply lumen to direct cooling fluid flow into the needle lumen so that liquid from the cooling flow vaporizes within the needle lumen to provide cooling to the nerve such that neuroma decreases in size and/or pain associated with the neuroma and experienced by the patient is reduced.

In some embodiments, the cooling flow may vaporize within the needle lumen to provide a cryozone having a cross-sectional area between 14-40 $mm^2$. In some embodiments, the cross-sectional area may be between 20-36 $mm^2$ or between 25-30 $mm^2$. The cryozone may be defined by a 0° C. isotherm (e.g., cooling zone). Optionally, the cooling flow may vaporize within the needle lumen to provide a cryozone having a volume between 65-105 $mm^3$, or between 80-90 $mm^3$.

The system may further include a heating element coupled with a proximal portion of the needle. The heating element may be configured to deliver heating phases to the skin of the patient. A processor may be configured to control the cooling fluid flow and the heating element in response to operator input. The processor may be configured to provide a treatment cycle in response to a treatment instruction. The treatment cycle may include at least one heating phase and one cooling phase. A degree of skin warmer throughout the treatment cycle may be provided. The degree of skin warmer may comprises 25-42° C. skin warmer throughout the treatment cycle. In some embodiments the skin warmer may be 30° C., 35° C., or 40° C.

The at least one heating phase may comprise a pre-warm phase with the heating element before the at least one cooling phase. The pre-warm phase may have a duration of 8-12 seconds or may end when the heating element reaches the skin warming temperature. The at least one cooling phase may have a duration between 20-65 seconds. In some embodiments, it may be beneficial to have shorter duration cooling phases. Some embodiments may provide sufficient treatment with a 30 second, 35 second, or 40 second cooling phase. In some embodiments, a 60 second cooling phase may be used.

In some embodiments, the at least one cooling phase may have a duration of less than 40 seconds. The 40 second cooling phase may be sufficient to create a cryozone having a cross-sectional area between 14-40 $mm^2$. In some embodiments, the at least one cooling phase may have a duration of less than 40 seconds and may create a cryozone having a volume between 65-105 $mm^3$.

Optionally, the at least one heating phase may also include a post-warm phase. The post-warm phase may have a duration of 12-18 seconds. Preferably, the distal portion of the needle may have a temperature of at least 0° C. at the end of the post-warm phase. In some embodiments, the needle may have a length of 5-14 mm. In some embodiments a 6-7 mm (e.g., 6.9 mm) needle may be used. In some embodiments where target tissues or nerves are deeper, one or more longer needles (e.g., 12 mm needle(s)) may be used. Optionally, the processor may be configured to provide an audio or visual alert at completion of a treatment cycle.

In further embodiments of the invention, a method for treating a neuroma, nerve entrapment, or other painful condition associated with a nerve in a limb of a patient is provided. The method may include identifying a location of pain experienced by the patient and associated with the neuroma and/or nerve entrapment. Thereafter, the method may include identifying the nerve based in-part on the identified location and positioning a distal end of a cryogenic cooling needle having a needle lumen proximal the nerve. A treatment cycle may then be delivered to the target tissue with the cryogenic cooling needle. The treatment cycle may comprise a cooling phase where cooling fluid flows into the needle lumen so that liquid from the cooling flow vaporizes within the needle lumen to provide cooling to the nerve such that the neuroma decreases in size and/or pain associated with the neuroma, nerve entrapment, or other painful condition is reduced.

In some embodiments, the treatment cycle may be configured to generate a cryozone having a cross-sectional area between 14-40 mm$^2$. The cryozone may be defined by a 0° C. isotherm. Optionally, the treatment cycle may be configured to generate a cryozone having a volume between 65-105 mm$^3$.

The method may include providing a degree of skin warmer throughout the delivery of the treatment cycle, the degree of skin warmer may be 20-42° C. skin warmer throughout the treatment cycle. Optionally, the cryogenic cooling needle may further comprises a heating element coupled with a proximal portion of the needle and the treatment cycle may further comprises at least one heating phase. The at least one heating phase may comprise a pre-warm phase with the heating element before the at least one cooling phase. The pre-warm phase may have a duration of 8-12 seconds.

The at least one cooling phase may have a duration of 20-65 seconds after the pre-warm phase. The at least one cooling phase may have a duration of less than 40 seconds and may be configured to create a cryozone having a cross-sectional area between 14-40 mm$^2$.

The at least one cooling phase may have a duration of less than 40 seconds and may create a cryozone having a volume between 65-105 mm$^3$.

In some embodiments the at least one heating phase further comprises a post-warm phase. The post-warm phase may have a duration of 12-18 seconds. Preferably, the distal portion of the needle may have a temperature of at least 0° C. at the end of the post-warm phase. In some embodiments, the needle may have a length of 5-12 mm.

In further embodiments, a system for reducing pain experienced by a patient is provided. The pain may be associated with a compressed nerve. The system may include a plurality of needles, each having a length between 5-14 mm and being spaced apart by not more than 3 mm. Each needle may further include a proximal end, an distal end, and a needle lumen therebetween. A heating element may be coupled with a proximal portion of the each of the plurality of needles. The heating element may be configured to deliver heating phases to the skin of the patient when the plurality of needles are inserted proximal to the nerve and a treatment cycle is being delivered to the nerve. A plurality of cooling fluid supply lumens may extend distally within the each of the plurality of needle lumens to a distal portion of each of the plurality of needle lumens. A cooling fluid source may be coupleable to the plurality of cooling fluid supply lumens to direct cooling fluid flow into the plurality of needle lumens so that liquid from the cooling flow vaporizes within the plurality of needle lumens to deliver adjacent cooling cycles to the nerve such that pain signals from the nerve are interrupted. A processor may be configured to control the cooling fluid flow and the heating element in response to operator input. In some embodiments the plurality of needles may be 27 gauge needles or smaller (e.g., 30 gauge needles). The plurality of needles may be 11-13 mm in length. Optionally, the plurality of needles may be 5-7 mm in length.

In further embodiments, a system for reducing pain experienced by a patient is provided. The pain may be associated with a compressed nerve. The system may include a first needle assembly. The first needle assembly may include a plurality of needles, each having a length between 10-14 mm and being spaced apart by not more than 3 mm (e.g., 2 mm). Each needle may further include a proximal end, an distal end, and a needle lumen therebetween. A second needle assembly may include a plurality of needles, each having a length between 5-7 mm and being spaced apart by not more than 3 mm (e.g., 2 mm). Each needle may further include a proximal end, an distal end, and a needle lumen therebetween.

A handle may have a needle assembly interface at a proximal end of the handle for receiving either the first needle assembly and the second needle assembly. A cooling fluid source may be housed in the handle and may be coupleable with the first needle assembly and the second needle assembly when attached to the handle to direct cooling fluid flow into the plurality of needle lumens so that liquid from the cooling flow vaporizes within the plurality of needle lumens to deliver adjacent cooling phases to the nerve such that pain associated with the compressed nerve is mitigated. A processor may be configured to control the cooling fluid flow in response to operator input.

Further features of the invention, its nature and various advantages will be more apparent from the accompanying drawings and the following detailed description.

DETAILED DESCRIPTION OF THE INVENTION

The present invention provides improved medical devices, systems, and methods. Embodiments of the invention may facilitate remodeling of target tissues disposed at and below the skin, optionally to treat pain associated with a sensory nerve. Embodiments of the invention may utilize a handheld refrigeration system that can use a commercially available cartridge of fluid refrigerant. Refrigerants well suited for use in handheld refrigeration systems may include nitrous oxide and carbon dioxide. These can achieve temperatures approaching −90° C.

Sensory nerves and associated tissues may be temporarily impaired using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a longer lasting treatment that limits or avoids inflammation and mobilization of skeletal muscle satellite repair cells. In some embodiments, axonotmesis with Wallerian degeneration of a sensory nerve is desired, which may be induced using treatment temperatures from about −20° C. to about −100° C. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling methods and devices may be found in commonly assigned U.S. Pat. No. 7,713,266 entitled "Subdermal Cryogenic Remodeling of Muscle, Nerves, Connective Tissue, and/or Adipose Tissue (Fat)", U.S. Pat. No. 7,850,683 entitled "Subdermal Cryogenic Remodeling of Muscles, Nerves, Connective Tissue, and/or Adipose Tissue (Fat)", U.S. Pat. No. 9,039,688 entitled "Method for Reducing Hyperdynamic Facial Wrinkles", and U.S. Pat. No. 8,298,216 entitled "Pain Management Using Cryogenic Remodeling," the full disclosures of which are each incorporated by reference herein.

Figure 1A:
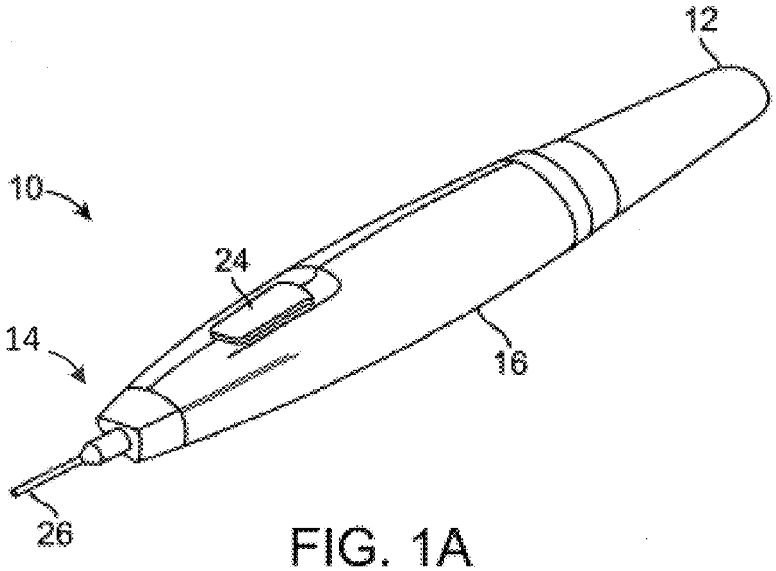
FIG. 1A is a perspective view of a self-contained subdermal cryogenic remodeling probe and system, according to some embodiments of the invention.
Figure 1B:
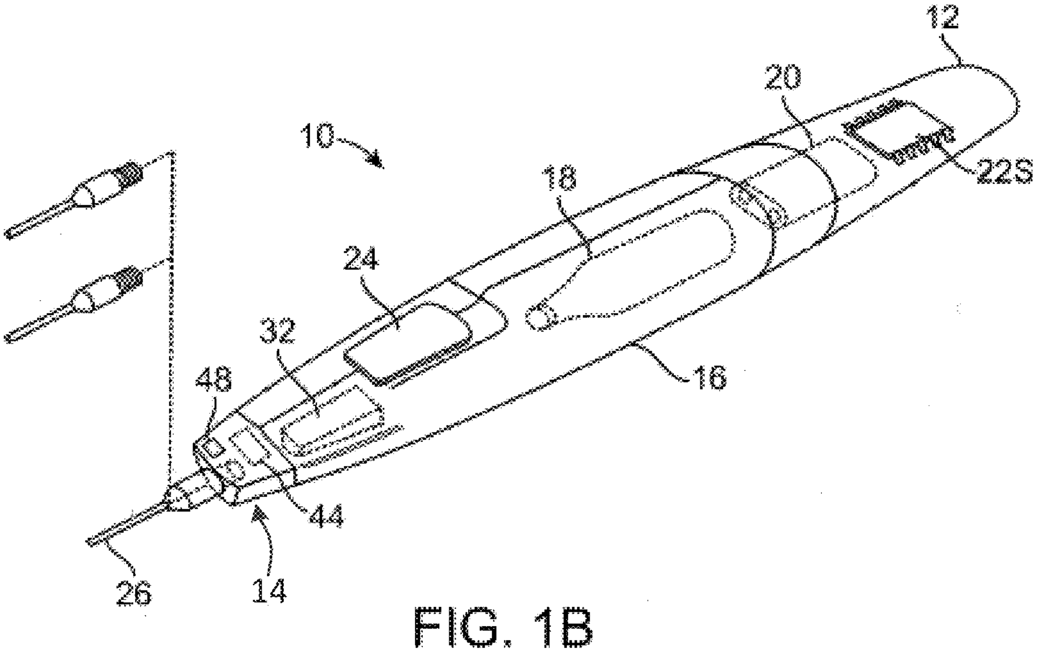
FIG. 1B is a partially transparent perspective view of the self-contained probe of FIG. 1A, showing internal components of the cryogenic remodeling system and schematically illustrating replacement treatment needles for use with the disposable probe according to some embodiments of the invention.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within housing 16, along with a circuit 22 having a processor for controlling cooling applied by self-contained system 10 in response to actuation of an input 24. Alternatively, electrical power can be applied through a cord from a remote power source. Power source 20 also supplies power to heater element 44 in order to heat the proximal region of probe 26 which may thereby help to prevent unwanted skin damage, and a temperature sensor 48 adjacent the proximal region of probe 26 helps monitor probe temperature. Additional details on the heater 44 and temperature sensor 48 are described in greater detail below. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may not be required.

Extending distally from distal end 14 of housing 16 may be a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 may comprise a 30 g needle having a sharpened distal end that is axially sealed. Probe 26 may have an axial length between distal end 14 of housing 16 and the distal end of the needle of between about 0.5 mm and 15 cm, preferably having a length from about 3 mm to about 10 mm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 may comprise a 16 g or smaller size needle, often comprising a 20 g needle or smaller, typically comprising a 25, 26, 27, 28, 29, or 30 g or smaller needle.

In some embodiments, probe 26 may comprise two or more needles arranged in a linear array, such as those disclosed in previously incorporated U.S. Pat. No. 7,850, 683. Another exemplary embodiment of a probe having multiple needle probe configurations allow the cryogenic treatment to be applied to a larger or more specific treatment area. Other needle configurations that facilitate controlling the depth of needle penetration and insulated needle embodiments are disclosed in commonly assigned U.S. Pat. No. 8,409,185 entitled "Replaceable and/or Easily Removable Needle Systems for Dermal and Transdermal Cryogenic Remodeling," the entire content of which is incorporated herein by reference. Multiple needle arrays may also be arrayed in alternative configurations such as a triangular or square array.

Arrays may be designed to treat a particular region of tissue, or to provide a uniform treatment within a particular region, or both. In some embodiments needle 26 may be releasably coupled with body 16 so that it may be replaced after use with a sharper needle (as indicated by the dotted line) or with a needle having a different configuration. In exemplary embodiments, the needle may be threaded into the body, press fit into an aperture in the body or have a quick disconnect such as a detent mechanism for engaging the needle with the body. A quick disconnect with a check valve may be advantageous since it may permit decoupling of the needle from the body at any time without excessive coolant discharge. This can be a useful safety feature in the event that the device fails in operation (e.g. valve failure), allowing an operator to disengage the needle and device from a patient's tissue without exposing the patient to coolant as the system depressurizes. This feature may also be advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 may comprise a canister, sometimes referred to herein as a cartridge, containing a liquid under pressure, with the liquid preferably having a boiling temperature of less than 37° C. at one atmosphere of pressure. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit coolant flow thereby regulating the temperature, treatment time, rate of temperature change, or other cooling characteristics. The valve will often be powered electrically via power source 20, per the direction of processor 22, but may at least in part be manually powered. The exemplary power source 20 comprises a rechargeable or single-use battery. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which are incorporated herein by reference.

The exemplary cooling fluid supply 18 may comprise a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2$a canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2A:
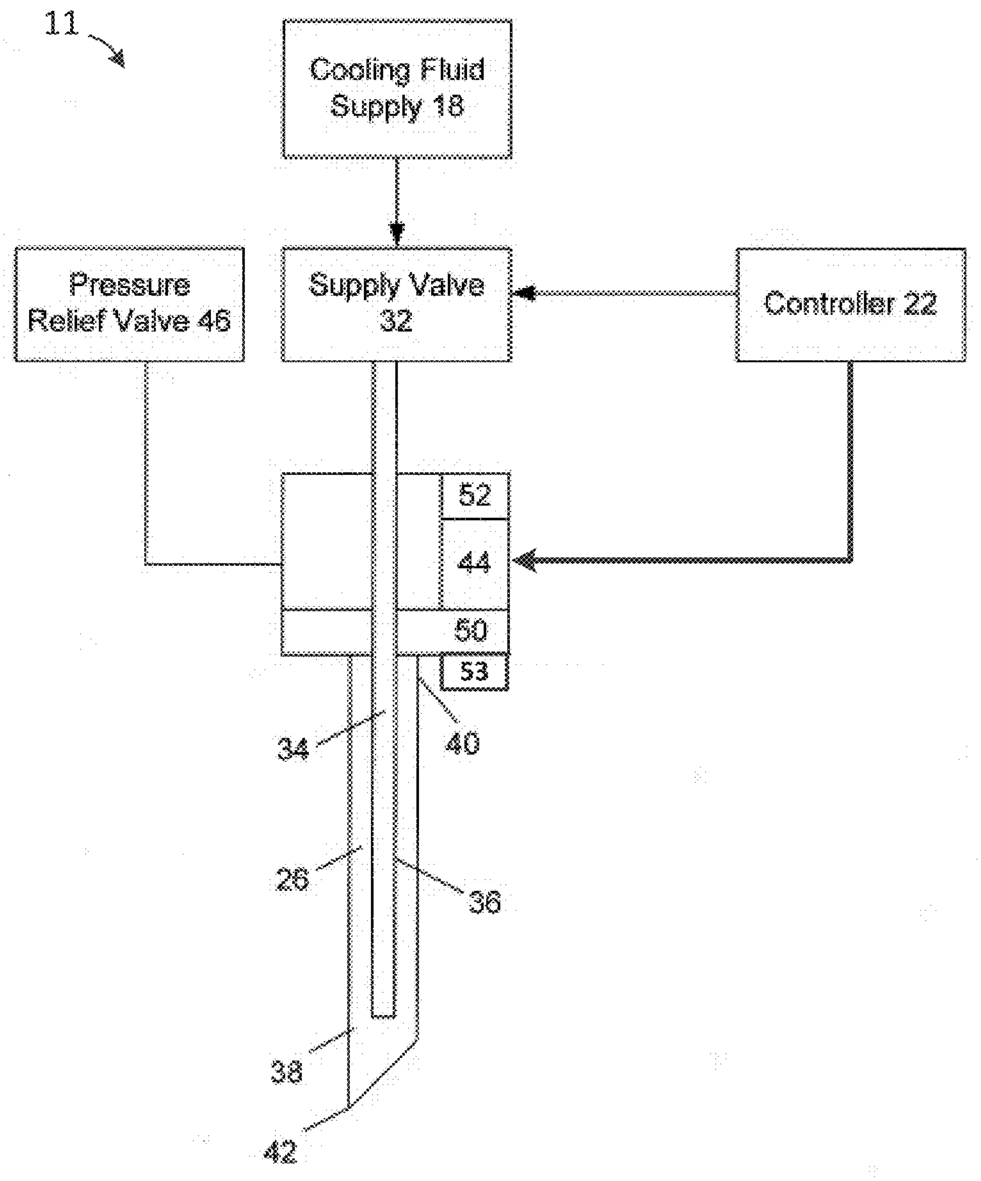
FIG. 2A schematically illustrates exemplary components that may be included in the treatment system.

Referring now to FIG. 2A, schematic 11 shows a simplified diagram of cryogenic cooling fluid flow and control. The flow of cryogenic cooling fluid from fluid supply 18 may be controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pat. No. 8,409,185.

Still referring to FIG. 2A, an optional heater (not illustrated) may be used to heat cooling fluid supply 18 so that heated cooling fluid flows through valve 32 and through a lumen 34 of a cooling fluid supply tube 36. In some embodiments a safety mechanism can be included so that the cooling supply is not overheated. Examples of such embodiments are disclosed in commonly assigned International Publication No. WO 2010075438, the entirety of which is incorporated by reference herein.

Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 μm, the inner diameter often being less than about 100 μm, and typically being less than about 40 μm. Exemplary embodiments of supply tube 36 have inner lumens of between about 15 and 50 μm, such as about 30 μm. An outer diameter or size of supply tube 36 will typically be less than about 1000 μm, often being less than about 800 μm, with exemplary embodiments being between about 60 and 150 μm, such as about 90 μm or 105 μm. The tolerance of the inner lumen diameter of supply tubing 36 will preferably be relatively tight, typically being about +/−10 μm or tighter, often being +/−5 μm or tighter, and ideally being +/−3 μm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Pat. No. 9,254,162 entitled "Dermal and Transdermal Cryogenic Microprobe Systems and Methods," the entire contents of which are incorporated herein by reference. Previously incorporated U.S. Pat. No. 8,409,185 also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve may allow better temperature control in the needle, minimizing transient temperatures. Further details on exhaust volume are disclosed in previously incorporated U.S. Pat. No. 8,409,185.

The heater 44 may be thermally coupled to a thermally responsive element 50, which is supplied with power by the controller 22 and thermally coupled to a proximal portion of the needle 26. The thermally responsive element 50 can be a block constructed from a material of high thermal conductivity and low heat capacity, such as aluminum. A first temperature sensor 52 (e.g., thermistor, thermocouple) can also be thermally coupled the thermally responsive element 50 and communicatively coupled to the controller 22. A second temperature sensor 53 can also be positioned near the heater 44, for example, such that the first temperature sensor 52 and second temperature sensor 53 are placed in different positions within the thermally responsive element 50. In some embodiments, the second temperature sensor 53 is placed closer to a tissue contacting surface than the first temperature sensor 52 is placed in order to provide comparative data (e.g., temperature differential) between the sensors 52, 53. The controller 22 can be configured to receive temperature information of the thermally responsive element 50 via the temperature sensor 52 in order to provide the heater 44 with enough power to maintain the thermally responsive element 50 at a particular temperature.

The controller 22 can be further configured to monitor power draw from the heater 44 in order to characterize tissue type, perform device diagnostics, and/or provide feedback for a tissue treatment algorithm. This can be advantageous over monitoring temperature alone, since power draw from the heater 44 can vary greatly while temperature of the thermally responsive element 50 remains relatively stable. For example, during treatment of target tissue, maintaining the thermally responsive element 50 at 40° C. during a cooling cycle may take 1.0 W initially (for a needle <10 mm in length) and is normally expected to climb to 1.5 W after 20 seconds, due to the needle 26 drawing in surrounding heat. An indication that the heater is drawing 2.0 W after 20 seconds to maintain 40° C. can indicate that an aspect of the system 10 is malfunctioning and/or that the needle 26 is incorrectly positioned. Correlations with power draw and correlated device and/or tissue conditions can be determined experimentally to determine acceptable treatment power ranges.

In some embodiments, it may be preferable to limit frozen tissue that is not at the treatment temperature, i.e., to limit the size of a formed cooling zone within tissue. Such cooling zones may be associated with a particular physical reaction, such as the formation of an ice-ball, or with a particular temperature profile or temperature volume gradient required to therapeutically affect the tissue therein. To achieve this, metering coolant flow could maintain a large thermal gradient at its outside edges. This may be particularly advantageous in applications for creating an array of connected cooling zones (i.e., fence) in a treatment zone, as time would be provided for the treatment zone to fully develop within the fenced in portion of the tissue, while the outer boundaries maintained a relatively large thermal gradient due to the repeated application and removal of refrigeration power. This could provide a mechanism within the body of tissue to thermally regulate the treatment zone and could provide increased ability to modulate the treatment zone at a prescribed distance from the surface of the skin. A related treatment algorithm could be predefined, or it could be in response to feedback from the tissue.

Such feedback could be temperature measurements from the needle 26, or the temperature of the surface of the skin could be measured. However, in many cases monitoring temperature at the needle 26 is impractical due to size constraints. To overcome this, operating performance of the sensorless needle 26 can be interpolated by measuring characteristics of thermally coupled elements, such as the thermally responsive element 50.

Additional methods of monitoring cooling and maintaining an unfrozen portion of the needle include the addition of a heating element and/or monitoring element into the needle itself. This could consist of a small thermistor or thermocouple, and a wire that could provide resistive heat. Other power sources could also be applied such as infrared light, radiofrequency heat, and ultrasound. These systems could also be applied together dependent upon the control of the treatment zone desired.

Alternative methods to inhibit excessively low transient temperatures at the beginning of a refrigeration cycle might be employed instead of or together with the limiting of the exhaust volume. For example, the supply valve 32 might be cycled on and off, typically by controller 22, with a timing sequence that would limit the cooling fluid flowing so that only vaporized gas reached the needle lumen 38 (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in previously incorporated U.S. Patent Pub. No. 2008/0154254.

Figure 2B:
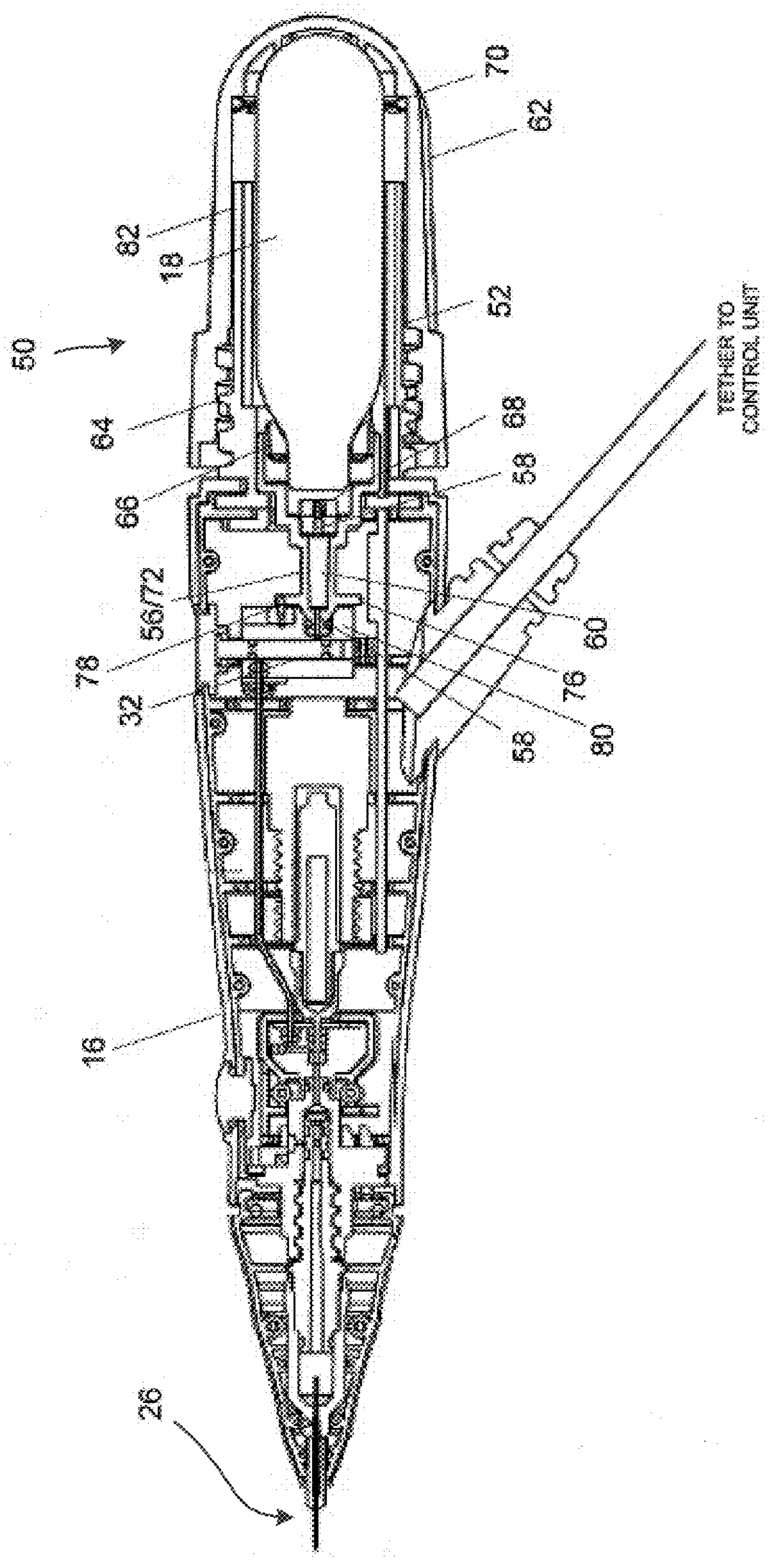
FIG. 2B is a cross-sectional view of the system of FIG. 1A, according to some embodiments of the invention.

FIG. 2B shows a cross-section of the housing 16. This embodiment of the housing 16 may be powered by an external source, hence the attached cable, but could alternatively include a portable power source. As shown, the housing includes a cartridge holder 50. The cartridge holder 50 includes a cartridge receiver 52, which may be configured to hold a pressured refrigerant cartridge 18. The cartridge receiver 52 includes an elongated cylindrical passage 54, which is dimensioned to hold a commercially available cooling fluid cartridge 18. A distal portion of the cartridge receiver 52 includes a filter device 56, which has an elongated conical shape. In some embodiments, the cartridge holder 50 may be largely integrated into the housing 16 as shown, however, in alternative embodiments, the cartridge holder 50 is a wholly separate assembly, which may be pre-provided with a coolant fluid source 18.

The filter device 56 may fluidly couple the coolant fluid source (cartridge) 18 at a proximal end to the valve 32 at a distal end. The filter device 56 may include at least one particulate filter 58. In the shown embodiment, a particulate filter 58 at each proximal and distal end of the filter device 56 may be included. The particulate filter 58 can be configured to prevent particles of a certain size from passing through. For example, the particulate filter 58 can be constructed as a microscreen having a plurality of passages less than 2 microns in width, and thus particles greater than 2 microns would not be able to pass.

The filter device 56 also includes a molecular filter 60 that is configured to capture fluid impurities. In some embodiments, the molecular filter 60 is a plurality of filter media (e.g., pellets, powder, particles) configured to trap molecules of a certain size. For example, the filter media can comprise molecular sieves having pores ranging from 1-20 Å. In another example, the pores have an average size of 5 Å. The molecular filter 60 can have two modalities. In a first mode, the molecular filter 60 will filter fluid impurities received from the cartridge 18. However, in another mode, the molecular filter 60 can capture impurities within the valve 32 and fluid supply tube 36 when the system 10 is not in use, i.e., when the cartridge 18 is not fluidly connected to the valve 32.

Alternatively, the filter device 56 can be constructed primarily from ePTFE (such as a GORE material), sintered polyethylene (such as made by POREX), or metal mesh. The pore size and filter thickness can be optimized to minimize pressure drop while capturing the majority of contaminants. These various materials can be treated to make it hydrophobic (e.g., by a plasma treatment) and/or oleophobic so as to repel water or hydrocarbon contaminants.

It has been found that in some instances fluid impurities may leach out from various aspects of the system 10. These impurities can include trapped moisture in the form of water molecules and chemical gasses. The presence of these impurities is believed to hamper cooling performance of the system 10. The filter device 56 can act as a desiccant that attracts and traps moisture within the system 10, as well as chemicals out gassed from various aspects of the system 10. Alternately the various aspects of the system 10 can be coated or plated with impermeable materials such as a metal.

Figure 2C:
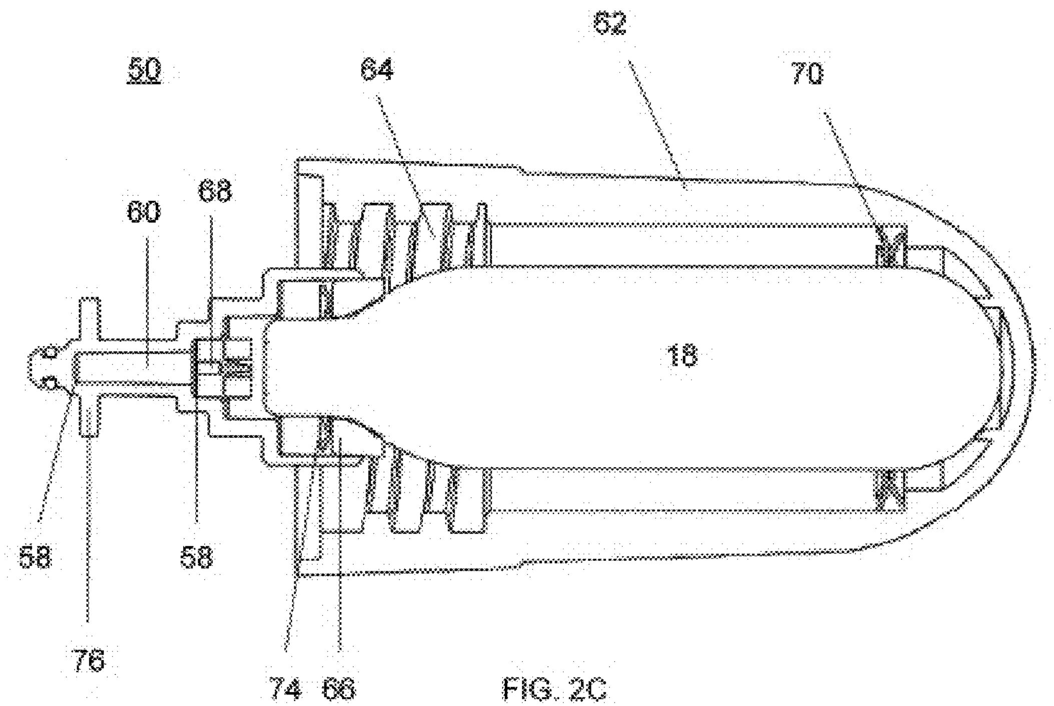
FIGS. 2C and 2D are cross-sectional views showing exemplary operational modes of the system of FIG. 2B.
Figure 2D:
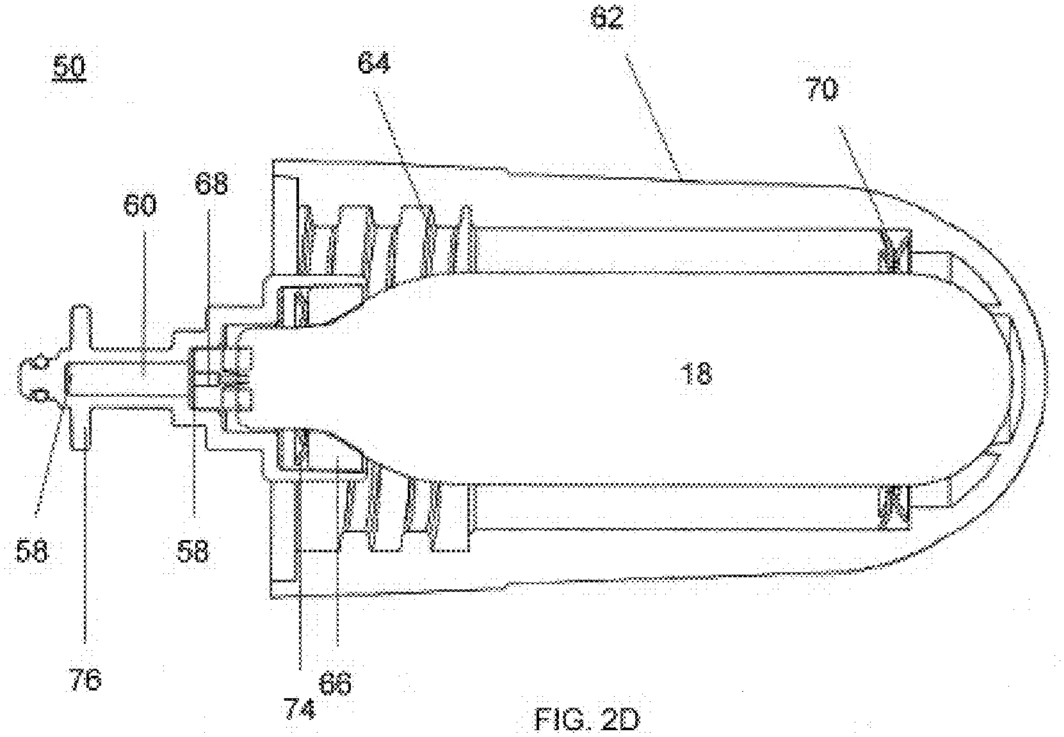

As shown in FIG. 2B and in more detail in FIG. 2C and FIG. 2D, the cartridge 18 can be held by the cartridge receiver 52 such that the cartridge 18 remains intact and unpunctured. In this inactive mode, the cartridge may not be fluidly connected to the valve 32. A removable cartridge cover 62 can be attached to the cartridge receiver 52 such that the inactive mode is maintained while the cartridge is held by the system 10.

In use, the cartridge cover 62 can be removed and supplied with a cartridge containing a cooling fluid. The cartridge cover 62 can then be reattached to the cartridge receiver 52 by turning the cartridge cover 62 until female threads 64 of the cartridge cover 62 engage with male threads of the cartridge receiver 52. The cartridge cover 62 can be turned until resilient force is felt from an elastic seal 66, as shown in FIG. 2C. To place the system 10 into use, the cartridge cover 62 can be further turned until the distal tip of the cartridge 18 is punctured by a puncture pin connector 68, as shown in FIG. 2D. Once the cartridge 18 is punctured, cooling fluid may escape the cartridge by flowing through the filter device 56, where the impurities within the cooling fluid may be captured. The purified cooling fluid then passes to the valve 32, and onto the coolant supply tube 36 to cool the probe 26. In some embodiments the filter device, or portions thereof, may be replaceable.

In some embodiments, the puncture pin connector 68 can have a two-way valve (e.g., ball/seat and spring) that is closed unless connected to the cartridge. Alternately, pressure can be used to open the valve. The valve closes when the cartridge is removed. In some embodiments, there may be a relief valve piloted by a spring which is balanced by high-pressure nitrous when the cartridge is installed and the system is pressurized, but allows the high-pressure cryogen to vent when the cryogen is removed. In addition, the design can include a vent port that vents cold cryogen away from the cartridge port. Cold venting cryogen locally can cause condensation in the form of liquid water to form from the surrounding environment. Liquid water or water vapor entering the system can hamper the cryogenic performance. Further, fluid carrying portions of the cartridge receiver 52 can be treated (e.g., plasma treatment) to become hydrophobic and/or oleophobic so as to repel water or hydrocarbon contaminants.

Figure 3A:
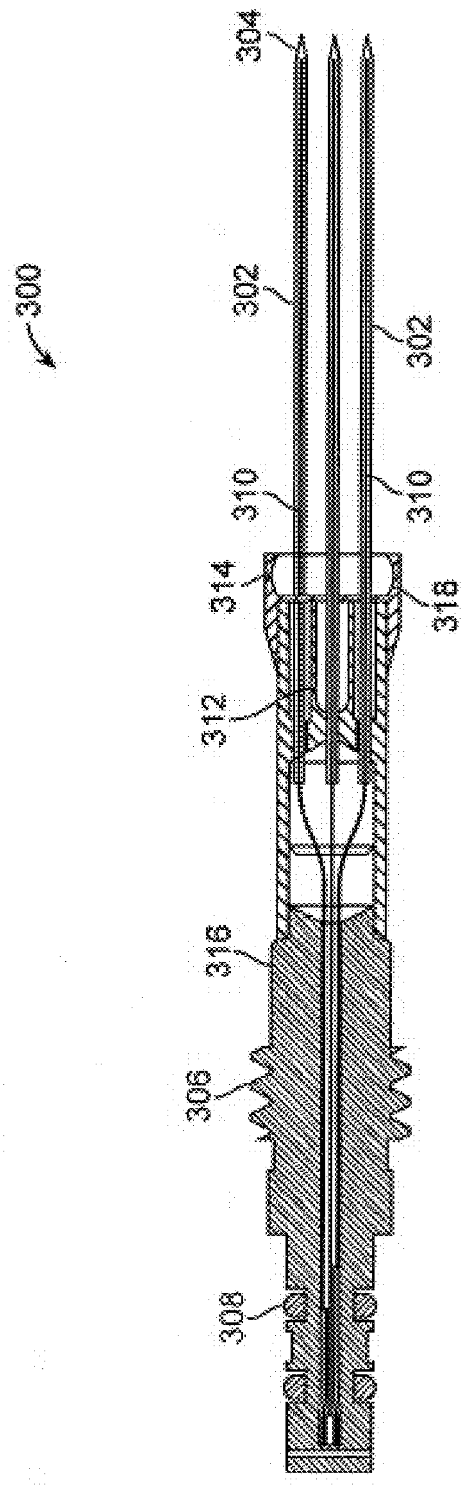
FIGS. 3A-3E illustrate an exemplary embodiment of a clad needle probe, according to some embodiments of the invention.
Figure 3B:
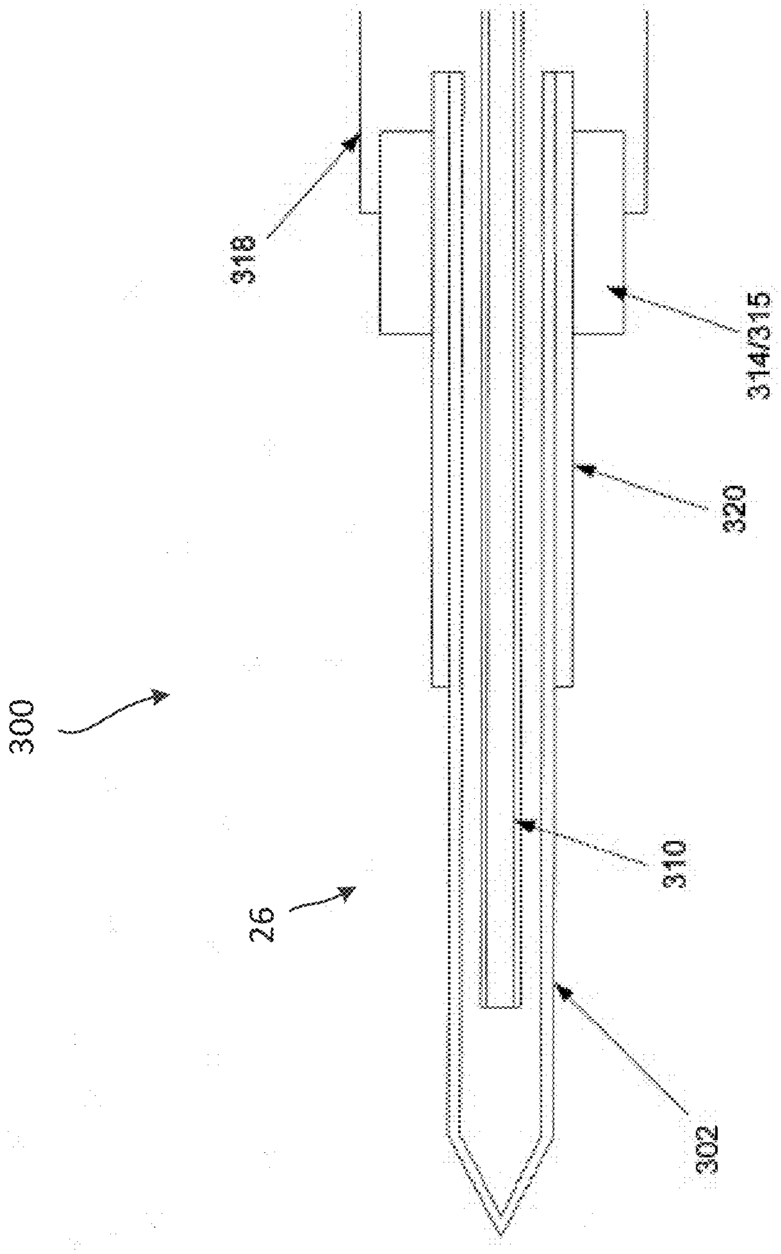

Turning now to FIG. 3A and FIG. 3B, an exemplary embodiment of probe 300 having multiple needles 302 is described. In FIG. 3A, probe housing 316 includes threads 306 that allow the probe to be threadably engaged with the housing 16 of a cryogenic device. O-rings 308 fluidly seal the probe housing 316 with the device housing 16 and prevent coolant from leaking around the interface between the two components. Probe 300 includes an array of three distally extending needle shafts 302, each having a sharpened, tissue penetrating tip 304. Using three linearly arranged needles allows a greater area of tissue to be treated as compared with a single needle. In use, coolant flows through lumens 310 into the needle shafts 302 thereby cooling the needle shafts 302. Ideally, only the distal portion of the needle shaft 302 would be cooled so that only the target tissue receives the cryogenic treatment. However, as the cooling fluid flows through the probe 300, probe temperature decreases proximally along the length of the needle shafts 302 towards the probe hub 318. The proximal portion of needle shaft 302 and the probe hub 318 contact skin and may become very cold (e.g. −20° C. to −25° C.) and this can damage the skin in the form of blistering or loss of skin pigmentation. Therefore it would be desirable to ensure that the proximal portion of needle shaft 302 and hub 318 remains warmer than the distal portion of needle shaft 302. A proposed solution to this challenge is to include a heater element 314 that can heat the proximal portion of needle shaft 302 and an optional temperature sensor 312 to monitor temperature in this region. To further this, a proximal portion of the needle shaft 302 can be coated with a highly thermally conductive material, e.g., gold, that is conductively coupled to both the needle shaft 302 and heater element 314. Details of this construction are disclosed below.

In the exemplary embodiment of FIG. 3A, resistive heater element 314 is disposed near the needle hub 318 and near a proximal region of needle shaft 302. The resistance of the heater element is preferably 1Ω to 1KΩ, and more preferably from 5Ω to 50Ω. Additionally, a temperature sensor 312 such as a thermistor or thermocouple is also disposed in the same vicinity. Thus, during a treatment as the needles cool down, the heater 314 may be turned on in order to heat the hub 318 and proximal region of needle shaft 302, thereby preventing this portion of the device from cooling down as much as the remainder of the needle shaft 302. The temperature sensor 312 may provide feedback to controller 22 and a feedback loop can be used to control the heater 314. The cooling power of the nitrous oxide may eventually overcome the effects of the heater, therefore the microprocessor may also be programmed with a warning light and/or an automatic shutoff time to stop the cooling treatment before skin damage occurs. An added benefit of using such a heater element is the fact that the heat helps to moderate the flow of cooling fluid into the needle shaft 302 helping to provide more uniform coolant mass flow to the needles shaft 302 with more uniform cooling resulting.

The embodiment of FIG. 3A illustrates a heater fixed to the probe hub. In other embodiments, the heater may float, thereby ensuring proper skin contact and proper heat transfer to the skin. Examples of floating heaters are disclosed in commonly assigned Int'l Pub. No. WO 2010/075448 entitled "Skin Protection for Subdermal Cryogenic Remodeling for Cosmetic and Other Treatments," the entirety of which is incorporated by reference herein.

In this exemplary embodiment, three needles are illustrated. One of skill in the art will appreciate that a single needle may be used, as well as two, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g. a rectangular array, a square array, elliptical, circular, triangular, etc.), and examples of three dimensional arrays include those where the needle tips are at different distances from the probe hub, such as in an inverted pyramid shape.

FIG. 3B illustrates a cross-section of the needle shaft 302 of needle probe 300. The needle shaft can be conductively coupled (e.g., welded, conductively bonded, press fit) to a conductive heater 314 to enable heat transfer therebetween. The needle shaft 302 is generally a small (e.g., 20-30 gauge) closed tip hollow needle, which can be between about 0.2 mm and 15 cm, preferably having a length from about 0.3 cm to about 1.5 cm. The conductive heater element 314 can be housed within a conductive block 315 of high thermally conductive material, such as aluminum and include an electrically insulated coating, such as Type III anodized coating to electrically insulate it without diminishing its heat transfer properties. The conductive block 315 can be heated by a resister or other heating element (e.g. cartridge heater, nichrome wire, etc.) bonded thereto with a heat conductive adhesive, such as epoxy. A thermistor can be coupled to the conductive block 315 with heat conductive epoxy allows temperature monitoring. Other temperature sensors may also be used, such as a thermocouple.

A cladding 320 of conductive material is directly conductively coupled to the proximal portion of the shaft of the needle 302, which can be stainless steel. In some embodiments, the cladding 320 is a layer of gold, or alloys thereof, coated on the exterior of the proximal portion of the needle shaft 302. In some embodiments, the exposed length of cladding 320 on the proximal portion of the needle is 2-100 mm. In some embodiments, the cladding 320 can be of a thickness such that the clad portion has a diameter ranging from 0.017-0.020 in., and in some embodiments 0.0182 in. Accordingly, the cladding 320 can be conductively coupled to the material of the needle 302, which can be less conductive, than the cladding 320. The cladding 320 may modify the lateral force required to deflect or bend the needle 26. Cladding 320 may be used to provide a stiffer needle shaft along the proximal end in order to more easily transfer force to the leading tip during placement and allow the distal portion of the needle to deflect more easily when it is dissecting a tissue interface within the body. The stiffness of needle 26 can vary from one end to the other end by other means such as material selection, metal tempering, variation of the inner diameter of the needle 26, or segments of needle shaft joined together end-to-end to form one contiguous needle 26. In some embodiments, increasing the stiffness of the distal portion of the needle 26 can be used to flex the proximal portion of the needle to access difficult treatment sites as in the case of upper limb spasticity where bending of the needle outside the body may be used to access a target peripheral nerve along the desired tissue plane.

In some embodiments, the cladding 320 can include sub-coatings (e.g., nickel) that promote adhesion of an outer coating that would otherwise not bond well to the needle shaft 302. Other highly conductive materials can be used as well, such as copper, silver, aluminum, and alloys thereof. In some embodiments, a protective polymer or metal coating can cover the cladding to promote biocompatibility of an otherwise non-biocompatible but highly conductive cladding material. Such a biocompatible coating however, would be applied to not disrupt conductivity between the conductive block 315. In some embodiments, an insulating layer, such as a ceramic material, is coated over the cladding 320, which remains conductively coupled to the needle shaft 302.

In use, the cladding 320 can transfer heat to the proximal portion of the needle 302 to prevent directly surrounding tissue from dropping to cryogenic temperatures. Protection can be derived from heating the non-targeting tissue during a cooling procedure, and in some embodiments before the procedure as well. The mechanism of protection may be providing heat to pressurized cryogenic cooling fluid passing within the proximal portion of the needle to affect complete vaporization of the fluid. Thus, the non-target tissue in contact with the proximal portion of the needle shaft 302 does not need to supply heat, as opposed to target tissue in contact with the distal region of the needle shaft 302. To help further this effect, in some embodiments the cladding 320 is coating within the interior of the distal portion of the needle, with or without an exterior cladding. To additionally help further this effect, in some embodiments, the distal portion of the needle can be thermally isolated from the proximal portion by a junction, such as a ceramic junction. While in some further embodiments, the entirety of the proximal portion is constructed from a more conductive material than the distal portion.

In use, it has been determined experimentally that the cladding 320 can help limit formation of a cooling zone to the distal portion of the needle shaft 302, which tends to demarcate at a distal end of the cladding 320. Accordingly, cooling zones are formed only about the distal portions of the needles. Thus, non-target tissue in direct contact with proximal needle shafts remain protected from effects of cryogenic temperatures. Such effects can include discoloration and blistering of the skin. Such cooling zones may be associated with a particular physical reaction, such as the formation of an ice-ball, or with a particular temperature required to therapeutically affect the tissue therein.

Standard stainless steel needles and gold clad steel needles were tested in porcine muscle and fat. Temperatures were recorded measured 2 mm from the proximal end of the needle shafts, about where the cladding distally terminates, and at the distal tip of the needles. Temperatures for clad needles were dramatically warmer at the 2 mm point versus the unclad needles, and did not drop below 4° C. The 2 mm points of the standard stainless steel needles almost equalize in temperature with the distal tip at temperatures below 0° C.

Figure 3C:
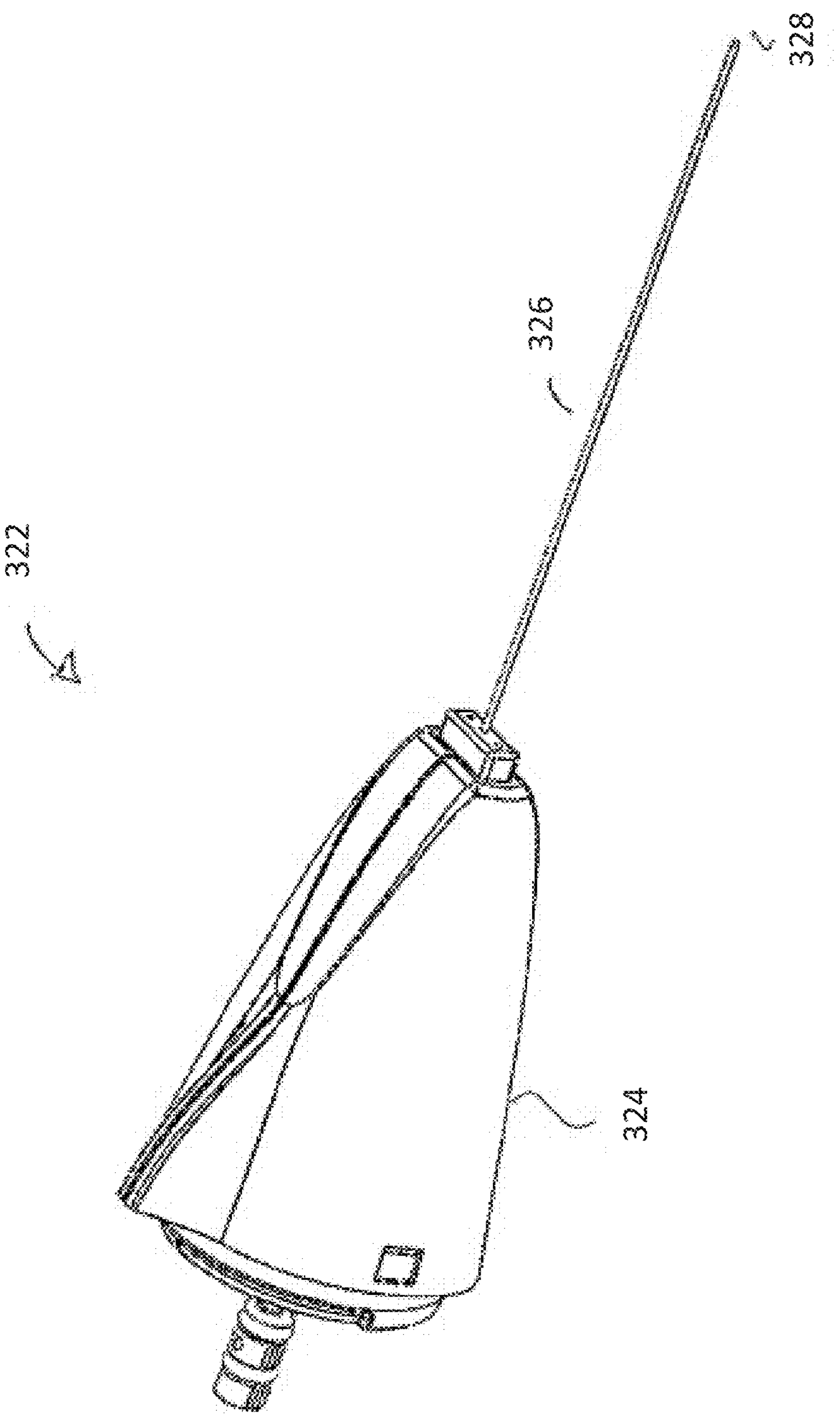
Figure 3D:
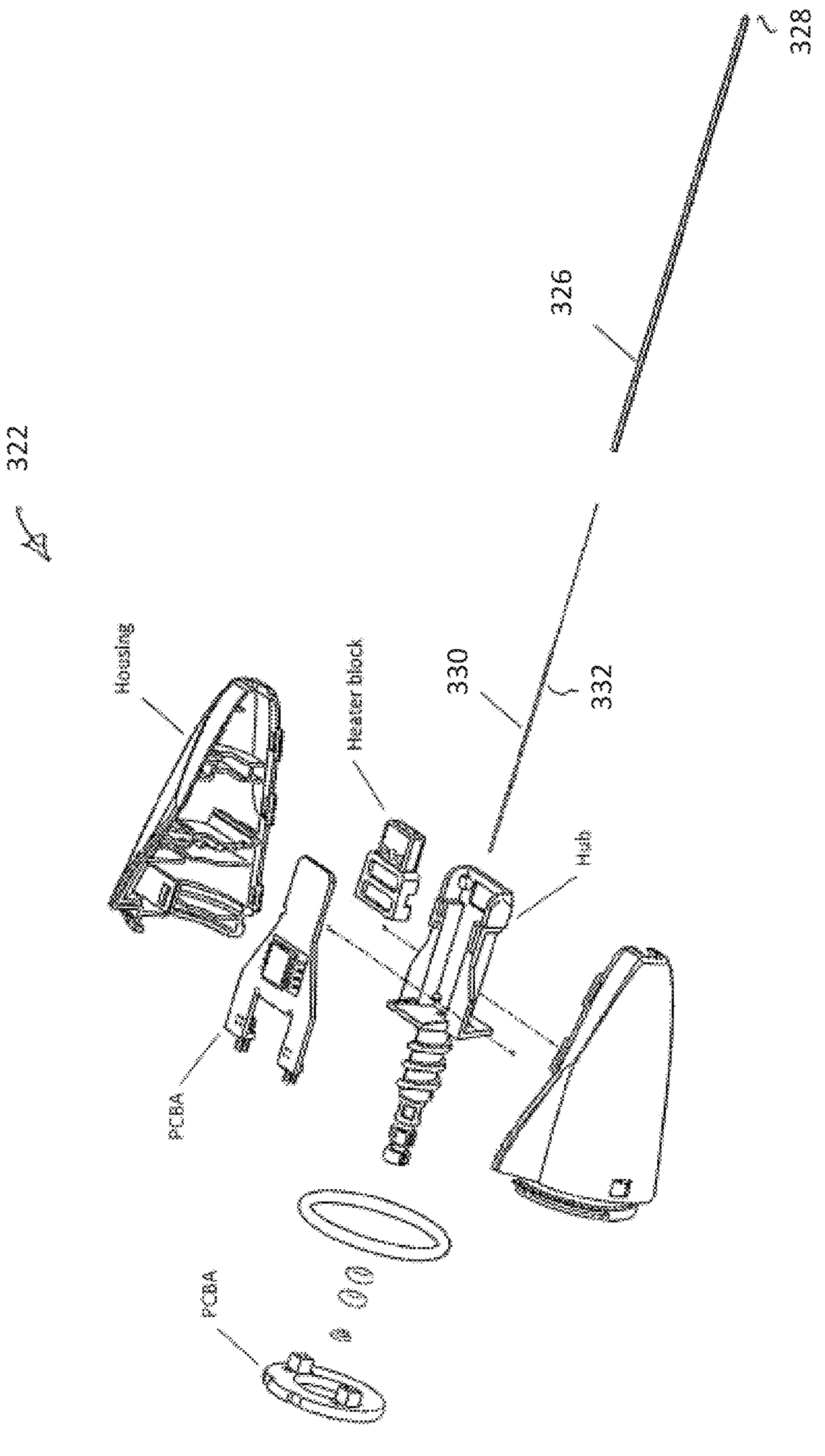

FIGS. 3C and 3D illustrates a detachable probe tip 322 having a hub connector 324 and an elongated probe 326. The probe tip 322 shares much of its construction with probe 300. However, the elongated probe 326 features a blunt tip 328 that is adapted for blunt dissection of tissue. The blunt tip 328 can feature a full radius tip, less than a full radius tip, or conical tip. In some embodiments, a dulled or truncated needle is used. The elongated probe 326 can be greater than 20 gauge in size, and in some embodiments range in size from 25-30 gauge. As with the embodiments described above, an internal supply tube 330 extends in cantilever. However, the exit of the supply tube 330 can be disposed at positions within the elongated probe 326 other than proximate the blunt tip 328. Further, the supply tube 330 can be adapted to create an elongated zone of cooling, e.g., by having multiple exit points for cryofluid to exit from.

The elongated probe 326 and supply tube 330 may be configured to resiliently bend in use, throughout their length at angles approaching 120°, with a 5-10 mm bend radius. This may be very challenging considering the small sizes of the elongated probe 326 and supply tube 330, and also considering that the supply tube 330 is often constructed from fused silica. Accordingly, the elongated probe 326 can be constructed from a resilient material, such as stainless steel, and of a particular diameter and wall thickness [0.004 to 1.0 mm], such that the elongated probe in combination with the supply tube 330 is not overly resilient so as to overtly resist manipulation, but sufficiently strong so as to prevent kinking that can result in coolant escaping. For example, the elongated probe can be 15 gauge or smaller in diameter, even ranging from 20-30 gauge in diameter. The elongated probe can have a very disparate length to diameter ratio, for example, the elongated probe can be greater than 30 mm in length, and in some cases range from 30-100 mm in length. To further the aforementioned goals, the supply tube 330 can include a polymer coating 332, such as a polyimide coating that terminates approximately halfway down its length, to resist kinking and aid in resiliency. The polymer coating 332 can be a secondary coating over a primary polyimide coating that extends fully along the supply tube. However, it should be understood that the coating is not limited to polyimide, and other suitable materials can be used. In some embodiments, the flexibility of the elongated probe 326 will vary from the proximal end to the distal end. For example, by creating certain portions that have more or less flexibility than others. This may be done, for example, by modifying wall thickness, adding material (such as the cladding discussed above), and/or heat treating certain portions of the elongated probe 326 and/or supply tube 330. For example, decreasing the flexibility of elongated probe 326 along the proximal end can improve the transfer of force from the hand piece to the elongated probe end for better feel and easier tip placement for treatment. The elongated probe and supply line 330 are may be configured to resiliently bend in use to different degrees along the length at angles approaching 120°, with a varying bend radius as small as 5 mm. In some embodiments, the elongated probe 326 will have external markings along the needle shaft indicating the length of needle inserted into the tissue.

Figure 3E:
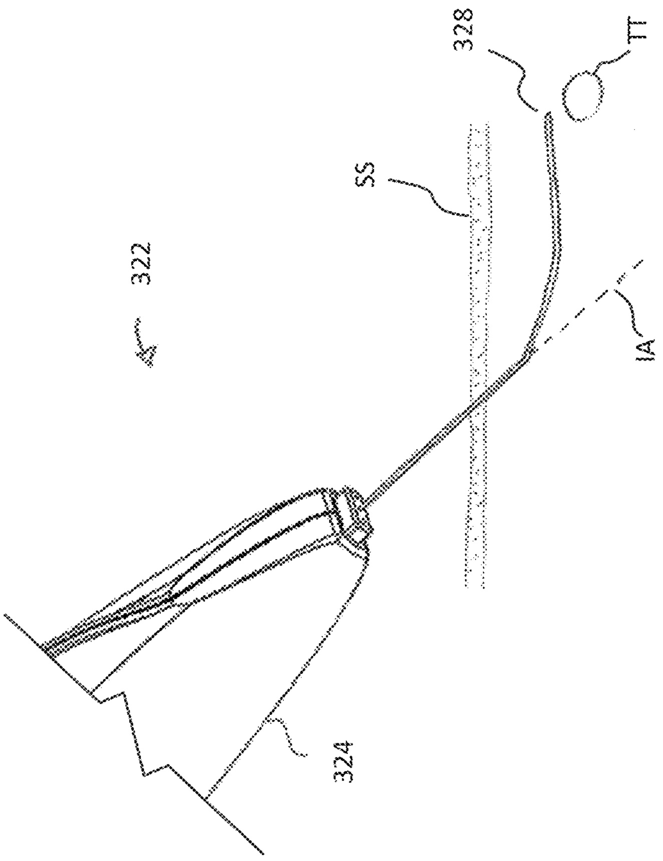

FIG. 3E illustrates an exemplary detachable probe tip 322 inserted through skin surface SS. As illustrated, the probe tip 322 is inserted along an insertion axis IA through the skin surface SS. Thereafter, the needle may be bent away from the insertion axis IA and advanced toward a target tissue TT in order to position blunt tip 328 adjacent to the target tissue TT. In some embodiments, the target tissue may be the infrapatellar branch of the saphenous nerve. In other embodiments the target tissue may be one or more branches of the anterior femoral cutaneous nerve or the lateral femoral cutaneous nerve.

In some embodiments, the probe tip 322 does not include a heating element, such as the heater described with reference to probe 300, since the effective treating portion of the elongated probe 326 (i.e., the area of the elongated probe where a cooling zone emanates from) is well laterally displaced from the hub connector 324 and elongated probe proximal junction. Embodiments of the supply tube are further described below and within commonly assigned U.S. Pub. No. 2012/0089211, which is incorporated by reference.

Figure 4A:
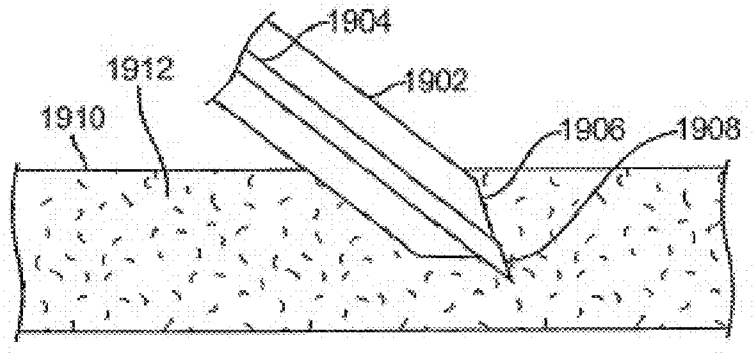
FIGS. 4A-4C illustrate an exemplary method of introducing a cryogenic probe to a treatment area, according to some embodiments of the invention.
Figure 4B:
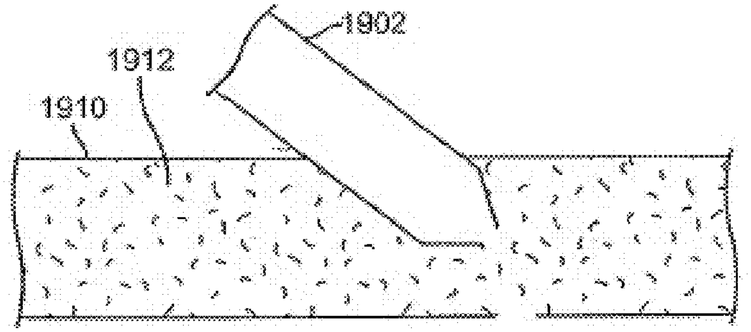
Figure 4C:
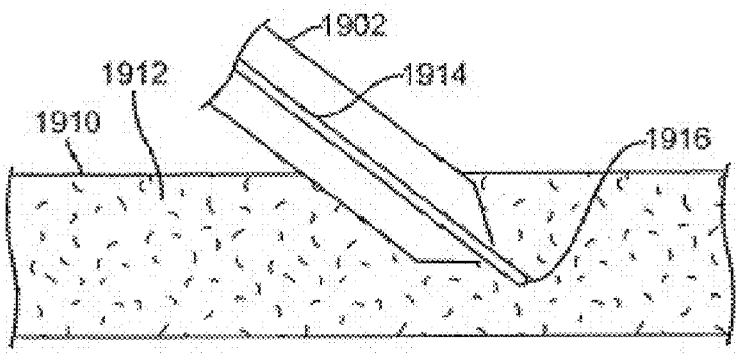

FIGS. 4A-4C illustrate an exemplary method of creating a hole through the skin that allows multiple insertions and positioning of a cryoprobe therethrough. In FIG. 4A a cannula or sheath 1902 is disposed over a needle 1904 having a tissue penetrating distal end 1908. The cannula may have a tapered distal portion 1906 to help spread and dilate the skin during insertion. The needle/sheath assembly is then advanced into and pierces the skin 1910 into the desired target tissue 1912. The inner pathway of the cannula or sheath 1902 may be curved to assist in directing the flexible needle 1904, or other probe, into a desired tissue layer coincident with the desired needle path in the tissue. Once the needle/sheath assembly has been advanced to a desired location, the needle 1904 may be proximally retracted and removed from the sheath 1902. The sheath now may be used as an easy way of introducing a cryoprobe through the skin without piercing it, and directing the cryoprobe to the desired target treatment area. FIG. 4B shows the sheath 1902 in position with the needle 1904 removed. FIG. 4C shows insertion of a cryoprobe 1914 into the sheath such that a blunt tip 1916 of the cryoprobe 1914 is adjacent the target treatment tissue. The cryoprobe may then be cooled and the treatment tissue cooled to achieve any of the cosmetic or therapeutic effects discussed above. In this embodiment, the cryoprobe preferably has a blunt tip 1916 in order to minimize tissue trauma. In other embodiments, the tip may be sharp and be adapted to penetrate tissue, or it may be round and spherical. The cryoprobe 1914 may then be at least partially retracted from the sheath 1902 and/or rotated and then re-advanced to the same or different depth and repositioned in sheath 1902 so that the tip engages a different portion of the target treatment tissue without requiring an additional piercing of the skin. The probe angle relative to the tissue may also be adjusted, and the cryoprobe may be advanced and retracted multiple times through the sheath so that the entire target tissue is cryogenically treated.

While the embodiment of FIGS. 4A-4C illustrates a cryoprobe having only a single probe, the cryoprobe may have an array of probes. Any of the cryoprobes described above may be used with an appropriately sized sheath. In some embodiments, the cryoprobe comprises a linear or two dimensional array of probes. Lidocaine or other local anesthetics may be used during insertion of the sheath or cryoprobe in order to minimize patient discomfort. The angle of insertion for the sheath may be anywhere from 0 to 180 degrees relative to the skin surface, and in specific embodiments is 15 to 45 degrees. The sheath may be inserted at any depth, but in specific embodiments of treating lines/wrinkles of the face, the sheath may be inserted to a depth of 1 mm to 10 mm, and more preferably to a depth of 2 mm to 5 mm.

Figure 4D:
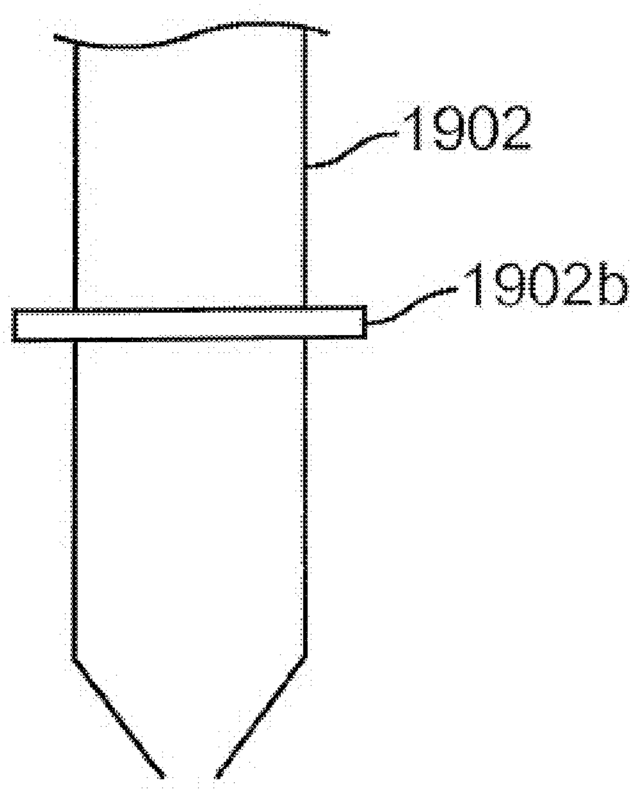
FIG. 4D illustrates an alternative exemplary embodiment of a sheath, according to some embodiments of the invention.

In an alternative embodiment seen in FIG. 4D, the sheath 1902 may include an annular flange 1902*b* on an outside surface of the sheath in order to serve as a stop so that the sheath is only inserted a preset amount into the tissue. The position of the flange 1902*b* may be adjustable or fixed. The proximal end of the sheath in this embodiment, or any of the other sheath embodiments may also include a one way valve such as a hemostasis valve to prevent backflow of blood or other fluids that may exit the sheath. The sheath may also insulate a portion of the cryoprobe and prevent or minimize cooling of unwanted regions of tissue.

Figure 5:
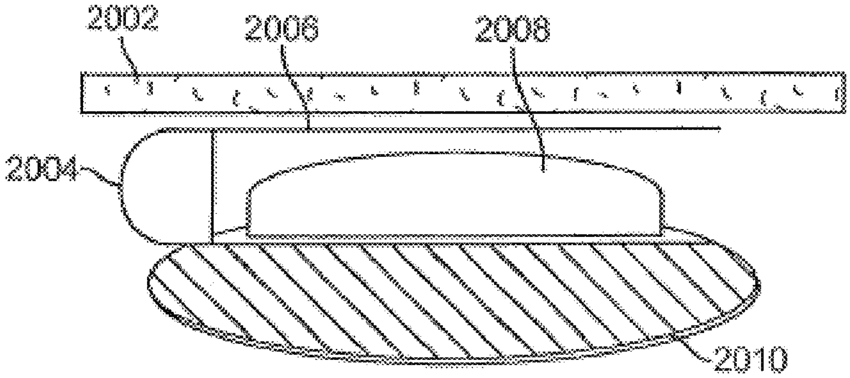
FIG. 5 illustrates an exemplary insulated cryoprobe, according to some embodiments of the invention.

Any of the cryoprobes described above may be used with the sheath embodiment described above (e.g. in FIGS. 3B, 4A-4C). Other cryoprobes may also be used with this sheath embodiment, or they may be used alone, in multi-probe arrays, or combined with other treatments. For example, a portion of the cryoprobe 2006 may be insulated as seen in FIG. 5. Cryoprobe 2006 includes a blunt tip 2004 with an insulated section 2008 of the probe. Thus, when the cryoprobe is disposed in the treatment tissue under the skin 2002 and cooled, the cryoprobe preferentially creates a cooling zone along one side while the other side remains uncooled, or only experiences limited cooling. For example, in FIG. 5, the cooling zone 2010 is limited to a region below the cryoprobe 2006, while the region above the cryoprobe and below the skin 2002 remain unaffected by the cooling.

Figure 6:
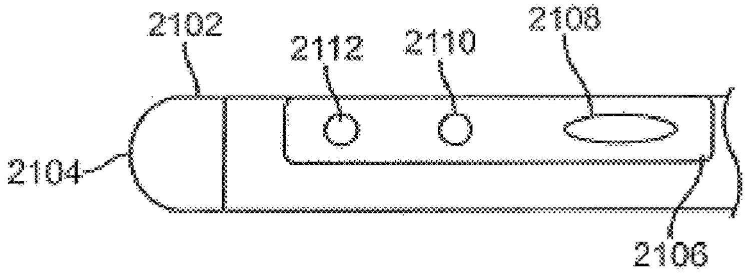
FIGS. 6-9 illustrate exemplary embodiments of cryofluid delivery tubes, according to some embodiments of the invention.
Figure 7:
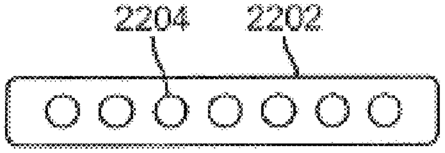
Figure 8:
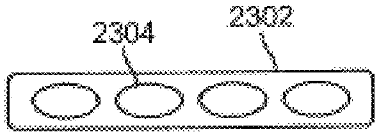
Figure 9:
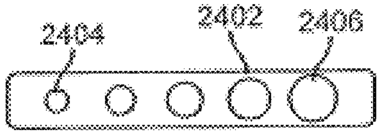

Different zones of cryotherapy may also be created by different geometries of the coolant fluid supply tube that is disposed in the cryoprobe. FIGS. 6-9 illustrate exemplary embodiments of different coolant fluid supply tubes. In FIG. 6 the coolant fluid supply tube 2106 is offset from the central axis of a cryoprobe 2102 having a blunt tip 2104. Additionally, the coolant fluid supply tube 2106 includes several exit ports for the coolant including circular ports 2110, 2112 near the distal end of the coolant fluid supply tube and an elliptical port 2108 proximal of the other ports. These ports may be arranged in varying sizes, and varying geometries in order to control the flow of cryofluid which in turn controls probe cooling of the target tissue. FIG. 7 illustrates an alternative embodiment of a coolant fluid supply tube 2202 having a plurality of circular ports 2204 for controlling cryofluid flow. FIG. 8 illustrates yet another embodiment of a coolant fluid supply tube 2302 having a plurality of elliptical holes 2304, and FIG. 9 shows still another embodiment of a coolant fluid supply tube 2402 having a plurality of ports ranging from smaller diameter circular holes 2404 near the distal end of the supply tube 2402 to larger diameter circular holes 2406 that are more proximally located on the supply tube 2402.

Figure 10:
FIG. 10 illustrates an example of blunt tipped cryoprobe, according to some embodiments of the invention.

As discussed above, it may be preferable to have a blunt tip on the distal end of the cryoprobe in order to minimize tissue trauma. The blunt tip may be formed by rounding off the distal end of the probe, or a bladder or balloon 2506 may be placed on the distal portion of the probe 2504 as seen in FIG. 10. A filling tube or inflation lumen 2502 may be integral with or separate from the cryoprobe 2504, and may be used to deliver fluid to the balloon to fill the balloon 2506 up to form the atraumatic tip.

Figure 11:
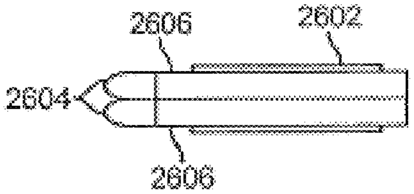
FIGS. 11 and 12 illustrate exemplary actuatable cryoprobes, according to some embodiments of the invention.
Figure 12:
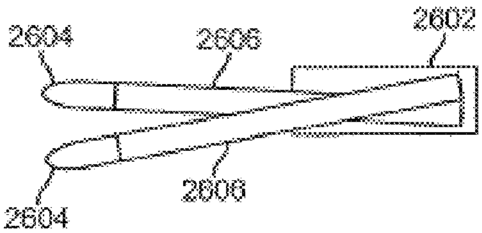

In some instances, it may be desirable to provide expandable cryoprobes that can treat different target tissues or accommodate different anatomies. For example, in FIGS. 11 and 12, a pair of cryoprobes 2606 with blunt tips 2604 may be delivered in parallel with one another and in a low profile through a sheath 2602 to the treatment area. Once delivered, the probes may be actuated to separate the tips 2604 from one another, thereby increasing the cooling zone. After the cryotherapy has been administered, the probes may be collapsed back into their low profile configuration, and retracted from the sheath.

In some embodiments, the probe may have a sharp tissue piercing distal tip, and in other embodiments, the probe may have a blunt tip for minimizing tissue trauma. To navigate through tissue, it may be desirable to have a certain column strength for the probe in order to avoid bending, buckling or splaying, especially when the probe comprises two or more probes in an array. One exemplary embodiment may utilize a variable stiff portion of a sleeve along the probe body to provide additional column strength for pushing the probe through tissue.

Figure 13:
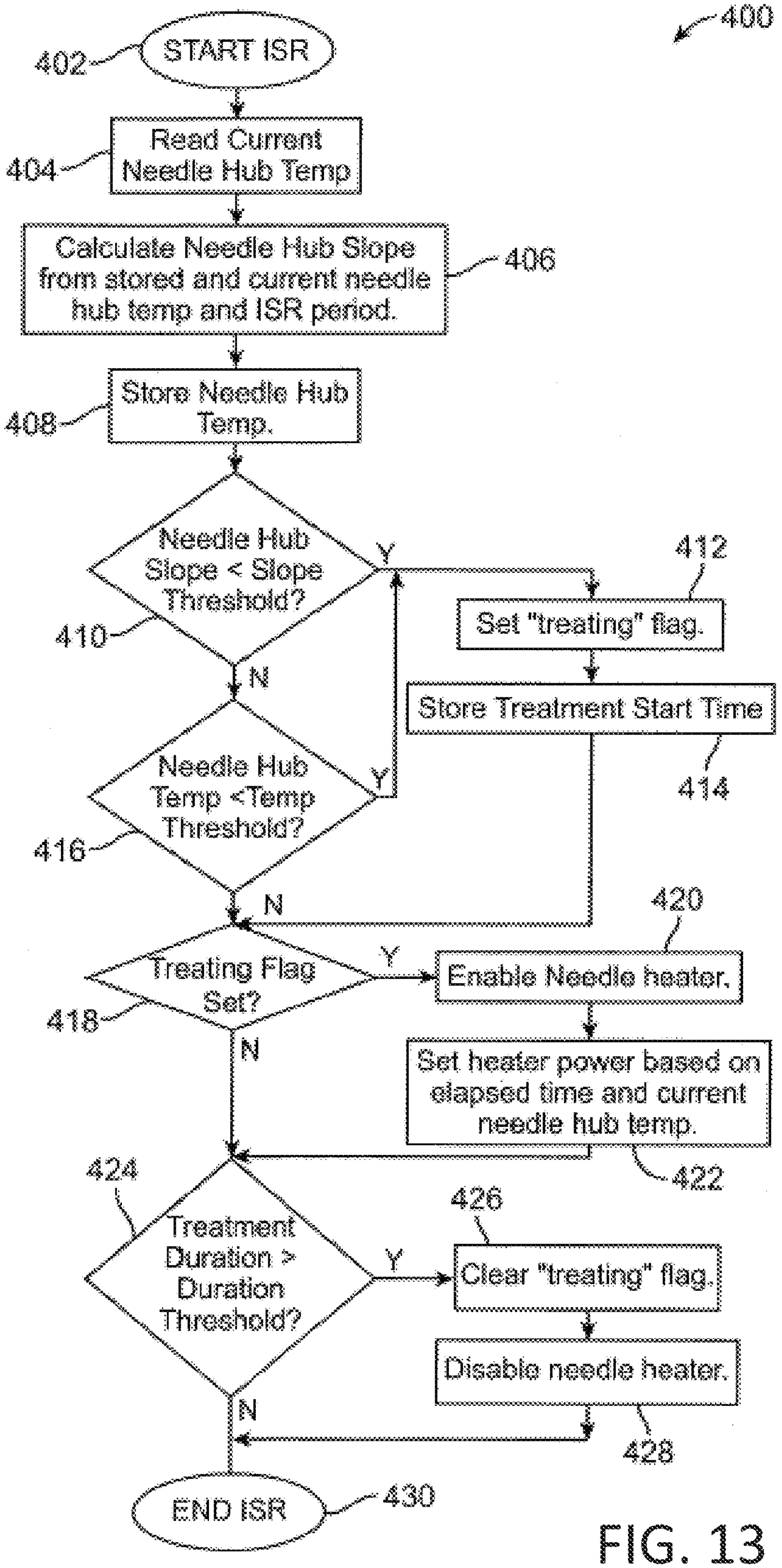
FIG. 13 is a flow chart illustrating an exemplary algorithm for heating the needle probe of FIG. 3A, according to some embodiment of the invention.

An exemplary algorithm 400 for controlling the heater element 314, and thus for transferring heat to the cladding 320, is illustrated in FIG. 13. In FIG. 13, the start of the interrupt service routine (ISR) 402 begins with reading the current needle hub temperature 404 using a temperature sensor such as a thermistor or thermocouple disposed near the needle hub. The time of the measurement is also recorded. This data is fed back to controller 22 where the slope of a line connecting two points is calculated. The first point in the line is defined by the current needle hub temperature and time of its measurement and the second point consists of a previous needle hub temperature measurement and its time of measurement. Once the slope of the needle hub temperature curve has been calculated 406, it is also stored 408 along with the time and temperature data. The needle hub temperature slope is then compared with a slope threshold value 410. If the needle hub temperature slope is less than the threshold value then a treating flag is activated 412 and the treatment start time is noted and stored 414. If the needle hub slope is greater than or equal to the slope threshold value 410, an optional secondary check 416 may be used to verify that cooling has not been initiated. In step 416, absolute needle hub temperature is compared to a temperature threshold. If the hub temperature is less than the temperature threshold, then the treating flag is activated 412 and the treatment start time is recorded 414 as previously described. As an alternative, the shape of the slope could be compared to a norm, and an error flag could be activated for an out of norm condition. Such a condition could indicate the system was not heating or cooling sufficiently. The error flag could trigger an automatic stop to the treatment with an error indicator light. Identifying the potential error condition and possibly stopping the treatment may prevent damage to the proximal tissue in the form of too much heat, or too much cooling to the tissue. The algorithm preferably uses the slope comparison as the trigger to activate the treatment flag because it is more sensitive to cooling conditions when the cryogenic device is being used rather than simply measuring absolute temperature. For example, a needle probe exposed to a cold environment would gradually cool the needle down and this could trigger the heater to turn on even though no cryogenic cooling treatment was being conducted. The slope more accurately captures rapid decreases in needle temperature as are typically seen during cryogenic treatments.

When the treatment flag is activated 418 the needle heater is enabled 420 and heater power may be adjusted based on the elapsed treatment time and current needle hub temperature 422. Thus, if more heat is required, power is increased and if less heat is required, power is decreased. Whether the treatment flag is activated or not, as an additional safety mechanism, treatment duration may be used to control the heater element 424. As mentioned above, eventually, cryogenic cooling of the needle will overcome the effects of the heater element. In that case, it would be desirable to discontinue the cooling treatment so that the proximal region of the probe does not become too cold and cause skin damage. Therefore, treatment duration is compared to a duration threshold value in step 424. If treatment duration exceeds the duration threshold then the treatment flag is cleared or deactivated 426 and the needle heater is deactivated 428. If the duration has not exceeded the duration threshold 424 then the interrupt service routine ends 430. The algorithm then begins again from the start step 402. This process continues as long as the cryogenic device is turned on.

Preferred ranges for the slope threshold value may range from about −5° C. per second to about −90° C. per second and more preferably range from about −30° C. per second to about −57° C. per second. Preferred ranges for the temperature threshold value may range from about 15° C. to about 0° C., and more preferably may range from about 0° C. to about 10° C. Treatment duration threshold may range from about 15 seconds to about 75 seconds.

It should be appreciated that the specific steps illustrated in FIG. 13 provide a particular method of heating a cryogenic probe, according to an embodiment of the present invention. Other sequences of steps may also be performed according to alternative embodiments. For example, alternative embodiments of the present invention may perform the steps outlined above in a different order. Moreover, the individual steps illustrated in FIG. 13 may include multiple sub-steps that may be performed in various sequences as appropriate to the individual step. Furthermore, additional steps may be added or removed depending on the particular applications.

Figure 14:
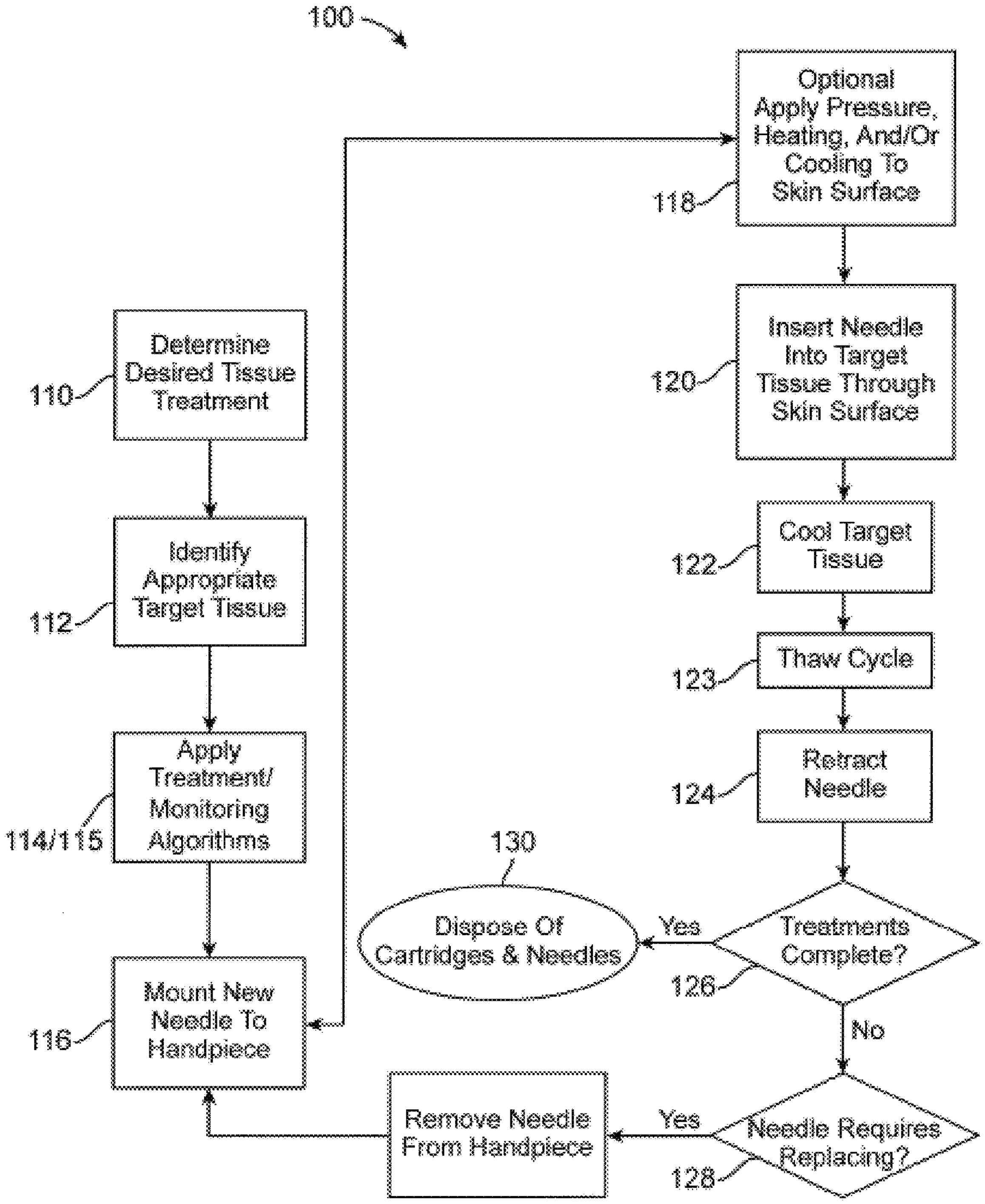
FIG. 14 is a flow chart schematically illustrating an exemplary method for treatment using the disposable cryogenic probe and system of FIGS. 1A and 1B, according to some embodiments of the invention.

The heating algorithm may be combined with a method for treating a patient. Referring now to FIG. 14, a method 100 facilitates treating a patient using a cryogenic cooling system having a reusable or disposable handpiece either of which that can be self-contained or externally powered with replaceable needles such as those of FIG. 1B and a limited capacity battery or metered electrical supply. Method 100 generally begins with a determination 110 of the desired tissue therapy and results, such as the inhibition of pain from a particular site. Appropriate target tissues for treatment are identified 112 (a tissue that transmits the pain signal), allowing a target treatment depth, target treatment temperature profile, or the like to be determined. Step 112 may include performing a tissue characterization and/or device diagnostic algorithm, based on power draw of system 10, for example.

The application of the treatment algorithm 114 may include the control of multiple parameters such as temperature, time, cycling, pulsing, and ramp rates for cooling or thawing of treatment areas. In parallel with the treatment algorithm 114, one or more power monitoring algorithms 115 can be implemented. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, heating, cooling, or combinations thereof may be applied 118 to the skin surface adjacent the needle insertion site before, during, and/or after insertion 120 and cryogenic cooling 122 of the needle and associated target tissue. Non-target tissue directly above the target tissue can be protected by directly conducting energy in the form of heat to the cladding on a proximal portion of the needle shaft during cooling. Upon completion of the cryogenic cooling cycle the needles will need additional "thaw" time 123 to thaw from the internally created cooling zone to allow for safe removal of the probe without physical disruption of the target tissues, which may include, but not be limited to nerves, muscles, blood vessels, or connective tissues. This thaw time can either be timed with the refrigerant valve shut-off for as short a time as possible, preferably under 15 seconds, more preferably under 5 seconds, manually or programmed into the controller to automatically shut-off the valve and then pause for a chosen time interval until there is an audible or visual notification of treatment completion.

Heating of the needle may be used to prevent unwanted skin damage using the apparatus and methods previously described. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used canister and/or needles can be disposed of 130. The handpiece may optionally be discarded.

As noted above, suitable target tissues can be selected that include a particular sensory nerve associated with pain, for example, such as: Myofascial, Fibromylagia, Lateral and Medial epicondylitis, Llio-hypo/llio-inguinal, Pudendal, Pyriformis, Osteo-Arthritis of the Knee, Patellar Tendonitis, Diabetic neuropathies, Carpal Tunnel, Phantom Limb, Migraine, Trigeminal Neuralgia, Occipital Neuralgia, Shoulder Arthritis, Shoulder Tendonitis, Suprascapular, Failed Back, Sciatica, Facet, Herniated Disc, Sacoiliac, Sciatic, Morton's Neuroma, and Plantar Fasciitis pain.

With respect to foot pain, sensory nerves of the foot may be targeted for treatment according to embodiments of the present invention. In some embodiments of the invention, nerve entrapment (also known as a pinched nerve) causing pain in the foot of a patient may be treated by targeting the associated sensory nerves of the foot with cooling treatment. Nerve entrapment may occur at various regions of the foot. A nerve entrapment is frequently caused by trauma, such as pressure created by swelling, excess pressure from a tight shoe, or blunt trauma. Symptoms of nerve entrapment include shooting, burning pain or sensitivity on the top portion of the foot.

Further, in some embodiments, devices and methods are provided for treatment of Morton's neuroma. Morton's neuroma is a disorder caused by digital nerve entrapment under the intermetatarsal ligament and results in benign thickening of the nerve. This occurs most commonly at the second and third intermetatarsal spaces (i.e., between the third and fourth toes). Symptoms include burning or shooting pain in the area between the third and fourth toes, most often with walking. Another common symptom is a vauge feeling of pressure beneath the toes, as if a sock was bunched-up underneath them. Morton's neuroma occurs more frequently in women, possibly because of the frequency of narrow or high-heeled shoe wear. Advantageously, cryogenic cooling of the neuroma may treat that neuroma rather than simply blocking pain signals. Additionally, forefoot neuropathy associated with gout may be treated in some embodiments.

Figure 15:
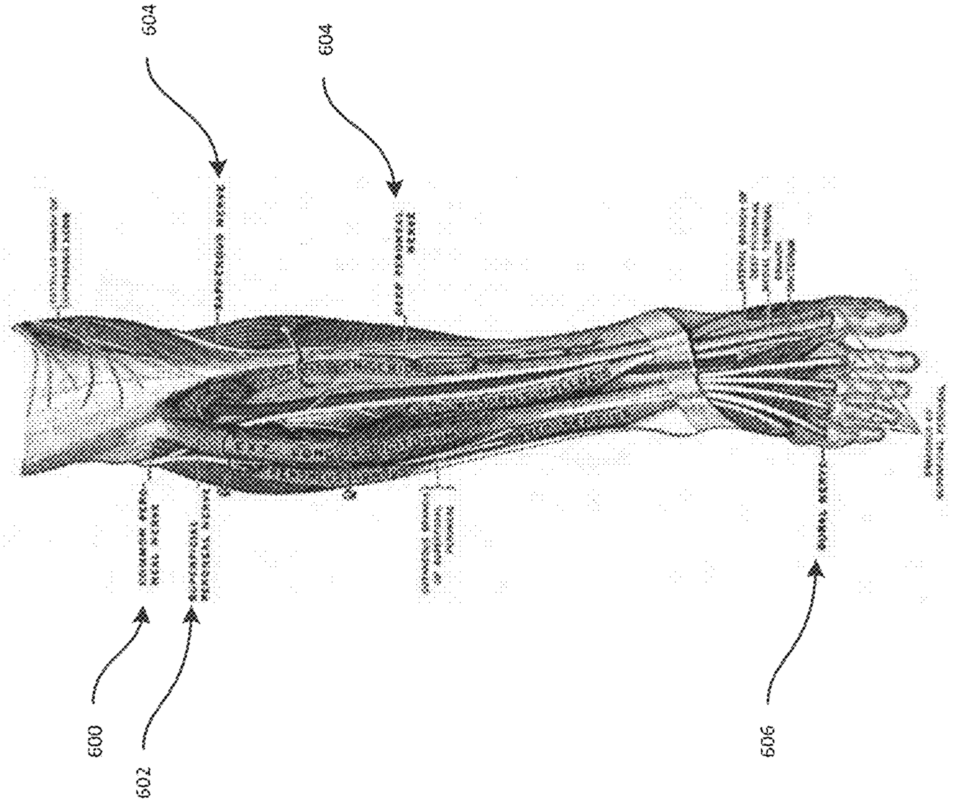
FIG. 15 illustrates the nerves of the lower leg and foot.

FIG. 15 illustrates the nerves of the lower leg and foot. The common fibular (peroneal) nerve 600 branches off the sciatic nerve in the popliteal region (behind the knee). It travels posterior to the head of the fibula to enter the lateral compartment of the leg. Here it divides into the superficial 602 and deep peroneal nerves 604.

Figure 16:
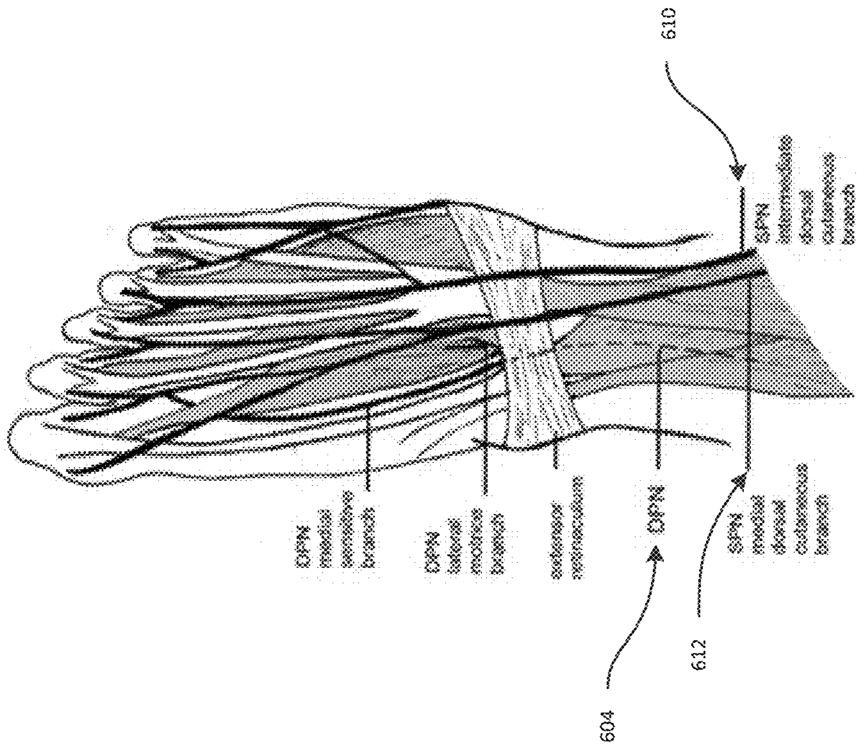
FIG. 16 shows the branching of the superficial peroneal nerve into the intermediate and medial cutaneous nerves.

The superficial peroneal nerve 602 runs through the lateral compartment of the leg and innervates the muscles in the lateral compartment and the skin over the anterior portion of the ankle and the dorsum of the foot. The superficial peroneal nerve 602 branches into the medial and intermediate dorsal cutaneous nerves. FIG. 16 shows the branching of the superficial peroneal nerve 602 into the intermediate 610 and medial cutaneous nerves 612.

The deep peroneal nerve 604 runs through extensor digitorum longus and down the interosseous membrane. It then crosses the tibia and enters the dorsum of the foot. The deep peroneal nerve 604 innervates the muscles in the anterior compartment of the leg and the dorsum of the foot. It also supplies the skin between the first and second toes.

Sural nerve 606 is formed by the union of branches from both the tibial and peroneal nerve and runs between the heads of the gastrocnemius, but it runs under the lateral malleolus. The Sural nerve 606 innervates the skin on the lateral side of the leg and foot.

Saphenous nerve 608 is a branch of the femoral nerve and runs down the medial portion of the leg to the medial part of the foot and innervates the skin on the medial side of the ankle and foot.

Figure 17B:
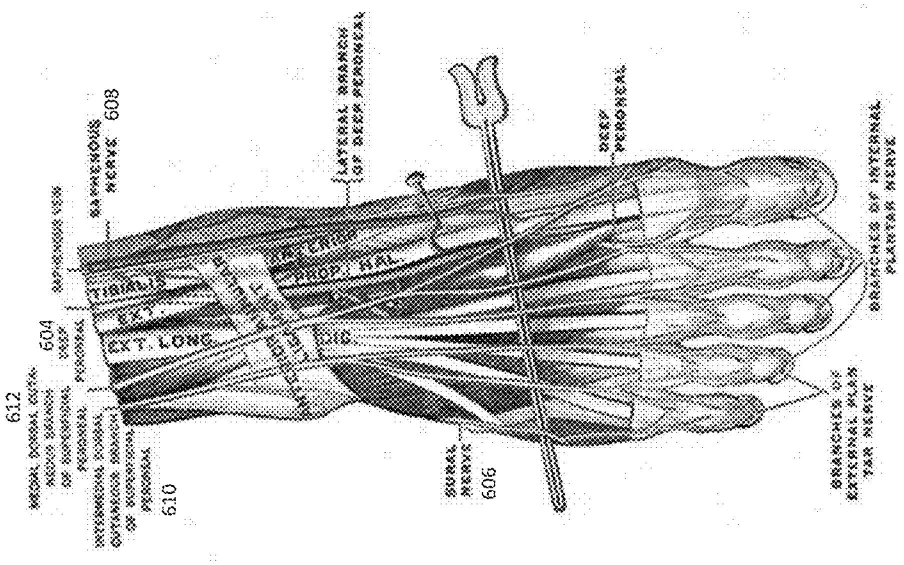
FIGS. 17A-17B show further details of nerves located in the foot.
Figure 17A:
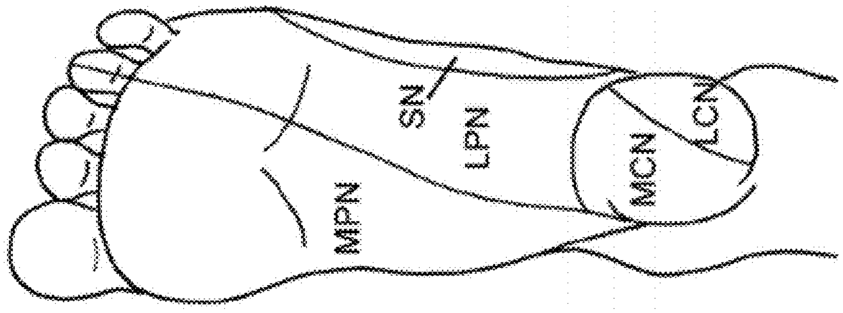

FIGS. 17A-17B show further details of nerves located in the foot. The tibial nerve 614 is a branch of the sciatic nerve. It runs down the leg, between the heads of the gastrocnemius, and passes under the soleus. It curves under the medial malleolus and continues into the foot. It innervates all the muscles in the posterior compartment of the leg. In the foot, it branches into the medial plantar nerve 616 and the lateral plantar nerve 618.

Medial plantar nerve 616 runs between the abductor halluces and flexor digitorum brevis in the foot. The medial plantar nerve 616 gives rights to digital branches 620 which then give rise to common digital branches 622 and finally, the terminal branches. This nerve 616 supplies the skin of the medial three and one-half digits. It innervates the skin on the medial side of the sole of the foot, and it is the nerve supply for some of the foot muscles. The medial plantar nerve 616 supplies the following muscles: abductor halluces, flexor digitorum brevis, flexor halluces brevis (in the third layer), and first lumbrical.

Lateral plantar nerve 618 runs between the quadratus plantae and flexor digitorum brevis. The lateral plantar nerve 618 gives rise to motor branches, a deep branch 624 and finally branches to the skin of the lateral one and one-half digits. It innervates the skin on the lateral part of the sole and several small muscles of the foot. The muscles supplied are the: abductor digiti minimi, accessory flexor (quadratus plantae), adductor halluces, flexor digiti minimi brevis, interossei, and lumbricals 3, 4, 5. Plantar digital nerves are nerves that branch of the medial and lateral plantar nerves 616, 618. Plantar digital nerves innervate the skin and nail beds of the toes.

Figure 18:
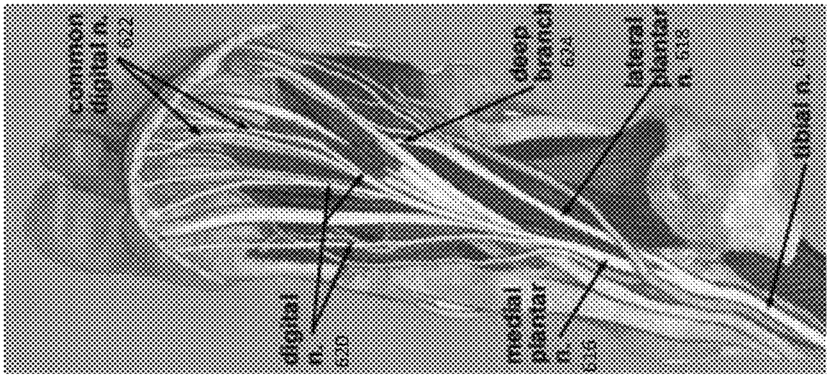
FIG. 18 shows innervation of the plantar aspect of the foot.

FIG. 18 shows innervation of the plantar aspect of the foot. The drawing illustrates the territories of the lateral calcaneal nerve (LCN), the latereal plantar nerve (LPN), the medial calcaneal nerve (MCN), the medial plantar nerve (MPN), and the sural nerve (SN).

Figure 19:
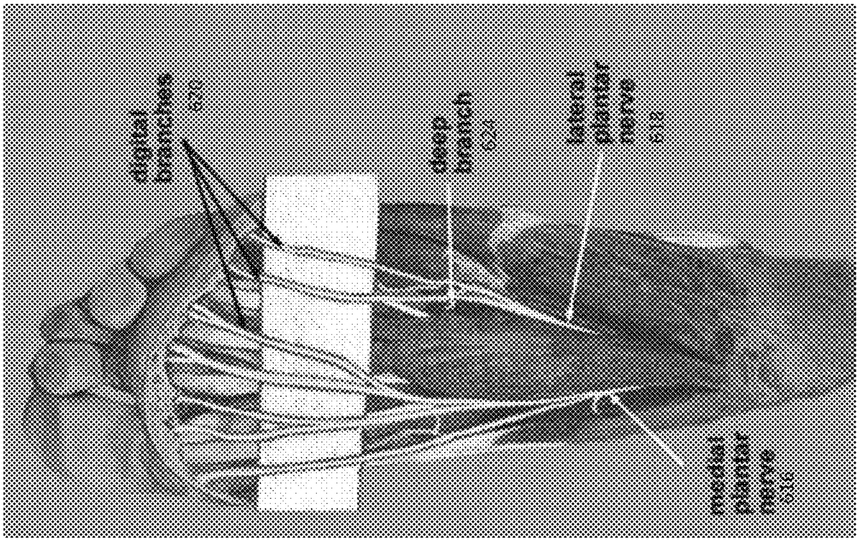
FIG. 19 shows the details of the intermediate dorsal cutaneous nerve.

FIG. 19 shows the details of the intermediate dorsal cutaneous nerve 610. The intermediate dorsal cutaneous nerve 610 is the term for the terminal/lateral branch of the peroneal nerve 602. The intermediate dorsal cutaneous nerve 610 is also called the external dorsal cutaneous branch. The intermediate dorsal cutaneous nerve 610 supplies the dorsal digital nerves and the foot dorsum to the toes (with the exception of sections of the first and second toes). The intermediate dorsal cutaneous nerve 610 travels through the dorsum's lateral side and splits into digital branches. The dorsal branches supply the common borders of the third, fourth, and fifth toes. The nerve lies near the sural nerve 606. The intermediate dorsal cutaneous nerve 616 sometimes communicates with the sural nerve 606. The intermediate dorsal cutaneous nerve 616 terminates near the terminal branches of the internal and external plantar nerves.

The medial dorsal cutaneous nerve 612 is the term for the terminal/medial branch of the peroneal nerve 602. The medial dorsal cutaneous nerve is also called the internal dorsal cutaneous branch. This nerve 612 supplies the medial digital nerves and the foot dorsum to the first, second, and third toes. The medial dorsal cutaneous nerve 612 travels through the center of the dorsum and splits into digital branches. The dorsal branches supply the common borders of the first, second, and third toes. The branches of the medial dorsal cutaneous nerve 612 terminate near the terminal branches of the deep peroneal nerve. The medial dorsal cutaneous nerve sometimes communicates with the deep peroneal nerve. The medial dorsal cutaneous nerve terminates near the terminal branches of the internal plantar nerves.

Figure 20:
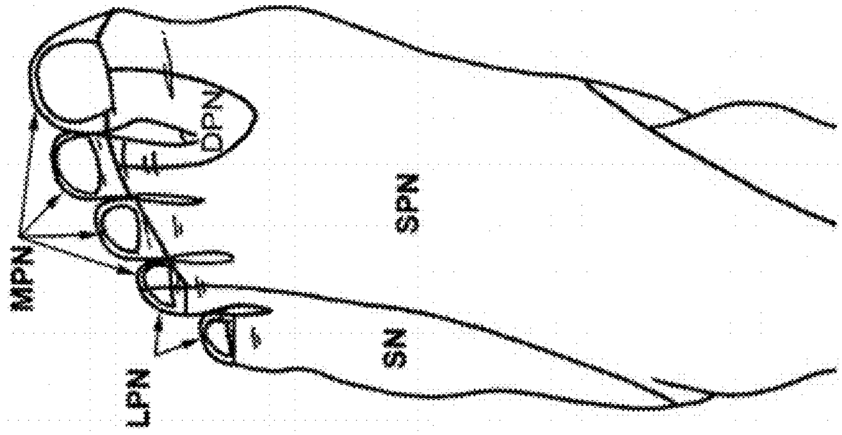
FIG. 20 is a drawing of the dorsal aspect of the foot and illustrates the territories of: the deep peroneal nerve (DPN), the lateral plantar nerve (LPN), the medial plantar nerve (MPN), the sural nerve (SN), and the superficial peroneal nerve (SPN) via the medial and intermediate cutaneous nerves.

FIG. 20 is a drawing of the dorsal aspect of the foot and illustrates the territories of: the deep peroneal nerve (DPN), the lateral plantar nerve (LPN), the medial plantar nerve (MPN), the sural nerve (SN), and the superficial peroneal nerve (SPN) via the medial and intermediate cutaneous nerves.

Figure 21:
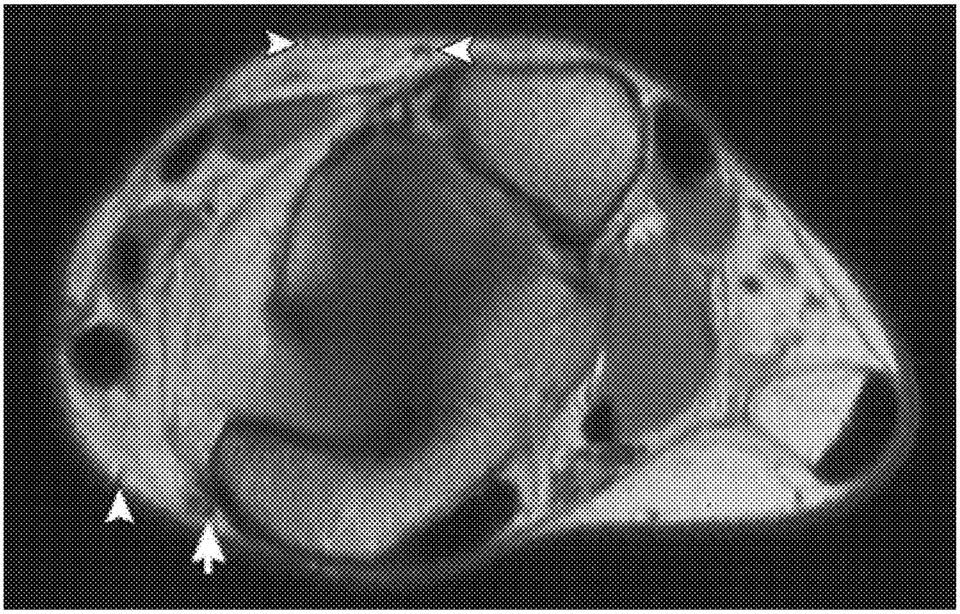
FIG. 21 shows an oblique coronal MR image of the subcutaneous superficial peroneal nerve branches and the great saphenous vein.

FIG. 21 shows an oblique coronal MR image. The MR image shows the subcutaneous superficial peroneal nerve branches (arrowheads) and the great saphenous vein (arrow).

Figure 22:
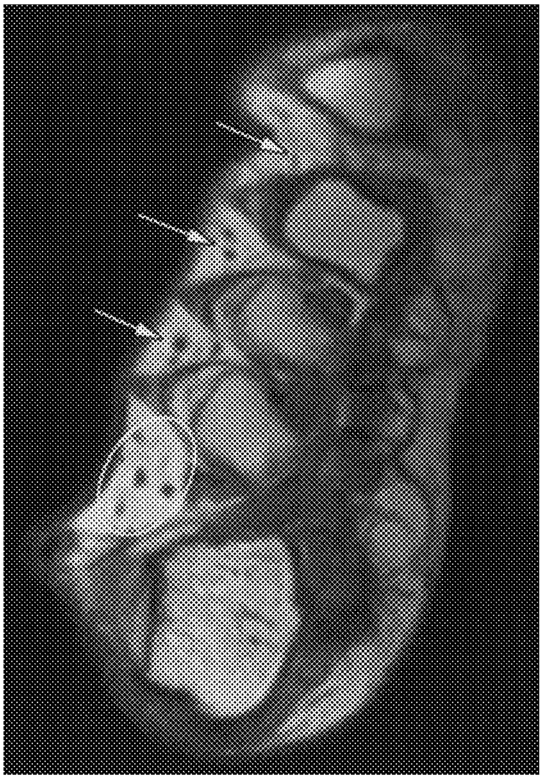
FIG. 22 shows a distal coronal MR image of the branches of the deep peroneal nerve for the first dorsal space.

FIG. 22 shows a distal coronal MR image. The distal coronal MR image demonstrates the branches of the deep peroneal nerve (DPN) for the first dorsal space (circled). The arrows indicate the second through the fourth dorsal spaces, and they also depict and the branches of the superficial peroneal nerve (SPN): the medial and intermediate cutaneous nerves.

Figure 23:
FIG. 23 shows another distal coronal MR image of the termination along the first toe of the medial cutaneous nerve and the medial plantar nerve.

FIG. 23 shows another distal coronal MR image. This distal coronal MR image shows the termination along the first toe of the medial cutaneous nerve (thin arrow) and the medial plantar nerve (thick arrow).

The target nerve may be accessed, for example, by locating adjacent landmarks and treating in a linear fashion to block the nerve at a desired location. In some embodiments, access to the target nerve may be gained by either a dorsal approach or plantar approach. In some cases it is advantageous treat an area proximal along the nerve from the neuroma or area of focused pain to extend the duration of treatment.

Studies were conducted to determine cryogenic cooling's effect on reducing forefoot pain. This prospective, non-randomized, interventional study enrolled seven Subjects with a diagnosis of forefoot pain related to nerve entrapment. Nine feet were treated.

The Visual Analogue Scale (VAS) is a 0 to 10 scale in which subjects rated pain. No pain equals zero and 10 equals very severe pain. The VAS was used by Subjects to assess pain pre-treatment, immediately post-treatment, at Day 7 and at Day 30.

Duration of treatment was assessed at Day 7, Day 30 and Day 56. At these time points, Subjects were asked if they were having an effect from the treatment. The Post-Treatment Questionnaire included 2 questions regarding subject satisfaction. Subjects were asked if he/she would recommend the treatment to a family member and would he/she have the treatment again if available. Both questions were answered with either a yes or a no.

Following the application of local anesthetic, the cryoprobe was inserted into the epidermis and advanced to the depth of the targeted nerve. FIGS. The associated sensory nerves may be in a treatment area distal to the superior extensor retinaculum (e.g., proximal portion of the anterior annular ligament) and may include: the intermediate, lateral, and medial dorsal cutaneous nerves; the sural nerve; the branches of the tibial nerve; and/or the deep peroneal nerve. A 15-second pre-warming phase was followed by treatment delivered for 60 seconds and a 10 second post-warming period, completed after treatment. Collectively this is described as a treatment cycle. The treatment was placed by first identifying the neuroma or area of focused pain by palpating the forefoot to identify the area of pain. After the treatment cycle was completed, the probe was placed adjacent to the previous treatment site to form a series of treatments across the pathway of the target nerve branch.

Seven Subjects were enrolled in the study and nine feet were treated. Table 1 provides an overview of subject accountability. Subjects with a diagnosis of bilateral forefoot pain due to nerve entrapment were eligible for a bilateral treatment. Two Subjects received bilateral treatment while five Subjects received unilateral treatment.

TABLE 1

Subject accountability overview

| Status | Site 16 | Site 18 | Total |
|---|---|---|---|
| Enrolled | 3 | 4 | 7 |
| Discontinued - subject withdrawal | 0 | 0 | 0 |
| Discontinued - investigator withdrawal | 0 | 0 | 0 |
| Excluded for Protocol Violation | 0 | 0 | 0 |
| Total Included in Data Analysis | 3 | 4 | 7 |

Subject accountability for required follow-up visits on Day 7 and Day 30 was 100% and 71% for the required follow-up visit at Day 56. The Day 56 follow-up visits were not done for Subjects 16-005 and 18-001. No Subjects were followed beyond Day 56. Table 2 provides an overview of subject accountability over follow-up periods. Subject 18-004 had an incomplete visit at Day 56; adverse event status and medications information were not collected.

TABLE 2

Subject Accountability over follow-up period

| Site ID | Enrolled | Treated | Day 7 | Day 30 | Day 56 |
|---|---|---|---|---|---|
| 16 | 3 | 3 | 3 | 3 | 2 |
| 18 | 4 | 4 | 4 | 4 | 3 |

Demographics—Of the Subjects enrolled, 57% (4/7) were male and 43% (3/7) were female. The average age was 54.6 years old (range 29-66 years old) with a standard deviation 12.1. The average VAS score at baseline was 6.3 (standard deviation 0.9). Demographics are detailed below in Table 3.

TABLE 3 demographics

| | Total |
|---|---|
| Gender (% M/% F) | 57%/43% |
| Average age (Standard deviation, range) | 54.6 (12.1, 29-66) |
| Average BMI (Standard deviation) | 29.3 (3.6) |
| Race (Subject reported) | 71% White<br>14% Native Hawaiian or Other Pacific Islander<br>14% Not reporting |
| Average baseline VAS (Standard deviation) | 6.3 (0.9) |

The cryogenic cooling device was used on awake subjects who were prepared with dermal anesthesia only. Local anesthesia was injected into target site with the goal of complete cutaneous anesthesia at the target treatment area prior to the treatment. All subjects received treatments with the Cryo-Touch III system, with either a 6 or 12 mm uncladded cryoprobe based on the Investigator's discretion. Anatomical landmarks and palpitation for pain were used to guide treatment locations. Landmarks comprised of palpation of metatarsal bones to locate intervening metatarsal spaces consistent with the target nerve pathway. Treatment algorithms were the same between sites. The sole difference was in treatment approach; at Site 16, the Investigator chose to approach the nerve dorsally, and at Site 18, the Investigator used a plantar approach. Subjects received an average of 3.7 insertions per side treated.

Effectiveness Results—VAS scores were analyzed for improvement in pain; response rates, minimal clinically important differences and statistically significant improvements from baseline were assessed at each follow-up point. Duration of treatment effect was analyzed for number of responders at each follow-up point. All averages calculated include the standard deviation parenthetically to better describe the statistical outcomes of this analysis.

VAS Score—Seventy-one percent (71%) of Subjects reported improvement in VAS at Day 7. Table 4 shows the percent of subjects with improvements in VAS score from the baseline. VAS scores were also assessed post-treatment and again at Day 30, with 100% (7/7) of subjects reporting improvement in VAS immediately post-treatment and 71% (5/7) with improvement at Day 30. The minimal clinically important difference (MCID) in VAS is 1.3 on the 0-100 mm scale, corresponding to a ≥2 point improvement on the 0-10 VAS scale used in this study. The percentage of Subjects showing a MCID in VAS was 100% (7/7) post-treatment, 71% (5/7) at Day 7 and 71% (5/7) at Day 30.

TABLE 4

Percent of subjects with improvement in VAS score from baseline.

| | Post Treatment | Day 7 | Day 30 |
|---|---|---|---|
| ≥1 point improvement | 100% (7/7) | 71% (5/7) | 71% (5/7) |
| ≥2 point improvement (MCID) | 100% (7/7) | 71% (5/7) | 71% (5/7) |

When assessed post-treatment, VAS scores improved by an average of 5.9 points (Table 5), an average of a 94% improvement from baseline. Table 5 shows the average improvement in VAS score from baseline. At Day 7, Subjects had an average VAS score improvement of 2.4 points, a 38% improvement from baseline. At Day 30 post-treatment, Subjects had an average VAS score improvement of 3 points, a 45% improvement compared to baseline.

TABLE 5

Average Improvement in VAS score from baseline.

| | Baseline (N = 7) | Post-Treatment (N = 7) | Day 7 (N = 7) | Day 30 (N = 7) |
|---|---|---|---|---|
| Average VAS Score (Standard deviation) | 6.3 (0.9) | 0.4 (0.7) | 3.9 (3.0) | 3.3 (1.9) |
| Average Point Improvement (Standard deviation) | | 5.9 (0.6) | 2.4 (3.2) | 3.0 (2.3) |
| Average Percent Improvement (Standard deviation) | | 94% (10%) | 38% (50%) | 45% (35%) |
| P-Value (Significance in change from baseline) | | 5.10E−07 | 0.03 | 0.61 |

Improvements in VAS scores from baseline to each time point were analyzed for statistical significance using a null hypothesis of $H_O$: Difference=0, where the difference is calculated by subtracting the score at post-treatment, Day 7 and Day 30 from the VAS score reported at baseline. A paired two-tailed t-test was employed to account for the possibility of subjects worsening over the course of the study, and the test was performed using a statistical significance level of $P<0.05$. The point improvements from baseline at post-treatment, Day 7 and Day 30 were tested against the null hypothesis and produced P-values of 5.10E-07, 0.03, and 0.61, respectively (Table 5). The P-values for post-treatment and Day 7 meet the threshold of statistical significance ($P<0.05$) and reject the null hypothesis of zero change from baseline. The analysis shows a statistically significant change in the VAS scores from baseline to these follow-up assessments. The P-value for the Day 30 results (0.61) does not meet the threshold of statistical significance ($P<0.05$) and therefore does not show a statistically significant change in VAS scores from baseline to the Day 30 follow-up.

Duration of Treatment Effect—Duration of treatment effect was assessed for subjects at Day 7, Day 30 and Day 56 on a per Subject basis. Additional duration of treatment assessments were completed via telephone call every four weeks until the Subject reported no effect up to 112 days post-treatment. At Day 7, 5/7 subjects (71%) reported continued effect from treatment (Table 6). Table 6 shows subjects reporting continued effect from treatment over initial follow-up period. At Day 30, 5/7 subjects (71%) reported continued effect from treatment. At Day 56, 3/5 subjects (60%) reported continued effect. Only one Subject was followed beyond Day 56 (see Section 5.5 Deviations from The Investigational Plan).

TABLE 6

Subjects reporting continued effect from treatment over initial follow-up period.

| | Day 7 | Day 30 | Day 56 |
|---|---|---|---|
| Reporting Effect from Treatment | 71% (5/7) | 71% (5/7) | 60% (3/5) |

Subjects completed the post-treatment questionnaire at Day 7 and Day 30 post-treatment visits. The questionnaire assessed subject satisfaction, subject experience with anticipated observations and subject's pain from treatment. The responses for subject satisfaction are shown in Table 7 below. At both Day 7 and Day 30, 5/7 Subjects (71%) said they would recommend the treatment to a family member. Similarly, 4/7 subjects (57%) would have the treatment again when asked at Day 7 and 5/7 (71%) said they would have the treatment again at Day 30.

TABLE 7

Subject Satisfaction

| | Day 7 | Day 30 |
|---|---|---|
| Would you recommend this treatment to a family member? (% Yes) | 71% (5/7) | 71% (5/7) |
| Would you have this treatment again? (% Yes) | 57% (4/7) | 71% (5/7) |

Subject experience with anticipated observations was assessed; the results are described in Table 8 below. The data below reflect how the Subjects responded to the question.

TABLE 8

Subject Reported anticipated observations

| | | Day 7 | Day 30 |
|---|---|---|---|
| Did the subject report any anticipated observations? (% Yes) | | 86% (6/7) | 57% (4/7) |
| If yes, how much did they/it impact subject's daily routine? | 1 (AO had very negative impact) | 17% (1/6) | 25% (1/4) |
| | 2 | 0% (0/6) | 0% (0/4) |
| | 3 | 17% (1/6) | 0% (0/4) |
| | 4 | 0% (0/6) | 25% (1/4) |
| | 5 (No impact at all) | 67% (4/6) | 50% (2/4) |

The Subject who rated their anticipated observations as having very negative impact reported severe tingling and moderate local pain at Day 7. At Day 30, the tingling had improved to moderate while pain remained moderate. This Subject did not complete a Day 56 visit.

Subjects were also asked if pain was present from treatment and if so, to rate it on a 1-5 scale. The results are shown below in Table 9.

TABLE 9

| Subject reported pain from treatment | | Day 7 | Day 30 |
|---|---|---|---|
| Is there any pain present from treatment? (% Yes) | | 71% (5/7) | 29% (2/7) |
| If yes, enter scale | 1 (Not at all painful) | 0% (0/5) | 50% (1/2) |
| | 2 | 60% (3/5) | 50% (1/2) |
| | 3 | 20% (1/5) | 0% (0/2) |
| | 4 | 20% (1/5) | 0% (0/2) |
| | 5 (Very painful) | 0% (0/5) | 0% (0/2) |

Entrapped nerves may be treated at the point of entrapment or proximal thereto. Wallerian degeneration of the nerve axons following focused cold therapy suspends conduction of entrapped nerve pain. Further, resulting inflammation may address the mechanism of entrapment so when the nerve axons regenerate they may no longer be entrapped and the chronic pain may not return.

Based on the high treatment response rate, a 27 ga 6-12 mm cryoprobe length for treatment of foot pain is possible. With needles less than 7 mm in length, larger gauge needles (smaller diameter) may be preferred so as to limit mechanical injury to the skin and tissue to be treated. For example, in some embodiments, it may be beneficial to use 27 gauge needles.

Optionally, longer needles may be used in some embodiments (e.g., 8-15 mm, 20 mm, 90 mm etc.). Longer needles may require a smaller gauge (larger diameter) needle so they have sufficient rigidity to maintain consistent spacing when placed deep in the tissue, but not so large as to create significant mechanical injury to the skin and tissue when inserted (e.g., greater than 20 ga). Alternate configurations of the device may have two or more needles spaced generally 3-5 mm apart of lengths ranging from up to 20 mm or greater, typically of 25 gauge or 23 gauge. Single needle configurations may be even longer (e.g., 90 mm) for reaching target tissues that are even deeper (e.g., >15 mm or so below the dermis). Longer needle devices (e.g., >10 mm) may not need active heating of the skin warmer and/or cladding found in designs using shorter needle(s) as the cooling zone may be placed sufficiently deep below the dermis to prevent injury. In some embodiments, devices with single long needle configurations may benefit from active nerve location such as ultrasound or electrical nerve stimulation to guide placement of the needle. Further, larger targets may require treatment from both sides to make sure that the cold zone created by the needle fully covers the target. Adjacent treatments placing the needle to either side of a nerve during two successive treatment cycles may still provide an effective treatment of the entire nerve cross-section.

In some situations, a probe with multiple spaced apart needles may be preferable (e.g., 2, 3, 4 or more). A device employing multiple needles may decrease the total treatment duration by creating larger cooling zones. Further, a multi-needle device may be configured to provide continuous cooling zones between the spaced apart needles. In some embodiments, the needles may be spaced apart by 1-5 mm. The spacing may be dependent on the type of tissue being targeted. For example, when targeting a nerve, it may be preferable to position the nerve between the two or more needles so that cooling zones are generated on both sides of the nerve. Treating the nerve from both sides may increase the probability that the entire cross-section of the nerve will be treated. For superficial peripheral nerves, the nerves may be at depths ranging from 2-6 mm and may be smaller in diameter, typically <2 mm. Accordingly, devices for treating foot pain and/or Morton's neuroma or other superficial peripheral nerves may comprises two or more 27 gauge needles spaced ≤2 mm apart and having typical lengths less than 7 mm (e.g., 6.9 mm); however longer needles may be required to treat the full patient population in order to access patients with altered nerve anatomy or patients with higher amounts of subcutaneous tissue such as those with high BMIs. Neuroma treatment may involve treating the neuroma directly. In some embodiments, it may be preferable to treat proximal to the neuroma so as to lead to a longer period of time required for nerve axon degeneration followed by nerve axon regeneration in the vicinity of the neuroma. Advantageously, focused cold therapy may relieve pain associated with neuroma in addition to reducing the size of the neuroma to relieve and/or cure the symptom.

Such treatments may also reduce the amount of drug therapy required, postpone invasive surgeries, and may provide an opportunity for physical rehabilitation (e.g., strength, flexibility, etc.). Furthermore the procedure may be used either pre- or post-operatively. Before total knee replacement surgery, the procedure may be used to limit pain, allow patients to strengthen the joint which may improve surgical outcomes. Post surgically, the procedure may be used to limit the use of opioids or other pain killers and or allow the patient to reduce residual post-surgical pain.

While the study used a treatment cycle comprising a 10 second pre-warm phase, followed by a 60 second cooling phase, followed thereafter by a 15 second post-warm phase with 40° C. skin warmer throughout, it should be understood that other treatment cycles may be implemented. In some embodiments, a pre-warming cycle can range from 0 to up to 30 seconds, preferably 5-15 seconds sufficient to pre-warm the cryoprobe and opposing skin. Treatment cooling may range from 5-120 seconds, preferably 15-60 seconds based on the flow rate, geometry of the cryoprobe, size of the therapy zone, size of the target nerve or tissue and the mechanism of action desired. Post warming can range from 0-60 seconds, preferably 10-15 seconds sufficient to return the cryoprobe to a steady state thermal condition and possibly to free the cryoprobe needle(s) from the frozen therapy zone (e.g., at least 0° C.) prior to removing the cryoprobe needles. For example, in some embodiments, devices with 6.9 mm long cladded needles may be warmed with a 30° C. heater. The treatment cycle may comprise a 10 second pre-warm phase, a 35 second cooling phase, and a 15 second post-warm phase. Advantageously, such a treatment cycle may make an equivalent cryozone as the treatment cycle used in the study in a shorter amount of time (e.g., a 35 second cooling phase compared to a 60 second cooling phase).

In some embodiments, treatment devices and treatment cycles may be configured to deliver a preferred cryozone volume. For example, in some embodiments, devices and treatment cycles may be configured to generate cryozones (defined by the 0 degree isotherm) having a cross-sectional area of approximately 14-55 $mm^2$ (e.g., 27 $mm^2$). Optionally, the devices and treatment cycles may be configured to generate cryozones having a volume of approximately 65-125 $mm^3$ (e.g., 85 $mm^3$).

Accordingly, in some embodiments, treatment cycles may be configured with cooling phases ranging between 15-75 seconds (e.g., 30 seconds, 35 seconds, 40 seconds, 45 seconds, etc.) depending on cooling fluid flow rates, warming phase durations, warming phase temperature, number of cooling needles, needle spacing, or the like in order to generate a desired cryozone. Similarly, treatment cycles may be configured with warming phases operating a temperatures ranging between 10-45° C. depending on the length of cooling phases, number of needles, needle spacing, etc. in order to generate a desired cryozone. Generally, with higher degree warming phases, the duration of the pre-warm phase and the cooling phase will be longer, however the post-warm phase duration may be reduced. In some embodiments the temperature can be set to one temperature during the pre-warm phase, another temperature during the cooling phase, and a third temperature during the post-warm phase.

In some embodiments, devices may be configured to limit flow rate of a cooling fluid to approximately 0.34-0.80 SLPM (gas phase). Optionally, in some embodiments, it may be preferable to configure the device and the treatment cycle to maintain the tip a less than −55° C. during cooling phases. In some embodiments, it may be preferable to configure the device and the treatment cycle to have the tip return to at least 0° C. at the end of the post-warm phase so as to ensure the device may be safely removed from the tissue after the treatment cycle.

While generally describing treatment cycles as including pre-heating/warming phases, it should be understood that other treatment cycles may not require a pre-heating/warming phase. For example, larger needle devices (e.g., 30-90 mm) may not require a pre-heat/warm phase. Larger needles may rely on the body's natural heat to bring the needle to a desired temperature prior to a cooling phase.

Although the above described procedures treated foot pain using cold, other methods and devices could be used to temporarily or permanently disable neuromas or fibromas. Examples include thermal nerve ablation such as with RF energy, or neurolysis using injections of phenol or ethyl alcohol.

In some embodiments of the present invention, treatment guidance can rely on rigid or boney landmarks because they are less dependent upon natural variations in body size or type, e.g. BMI. Soft tissues, vasculature and peripheral nerves pass adjacent to the rigid landmarks because they require protection and support. The target nerve to relieve pain can be identified based on the diagnosis along with patients identifying the area of pain, biomechanical movements that evoke pain from specific areas, palpation, and diagnostic nerve blocks using an temporary analgesic (e.g. 1-2% Lidocaine). Target nerve (tissue) can be located by relying on anatomical landmarks to indicate the anatomical area through which the target nerve (tissue) reside. Alternatively, nerve or tissue locating technologies can be used. In the case of peripheral nerves, electrical stimulation or ultrasound can be used to locate target nerves for treatment. Electrical nerve stimulation can identify the nerve upon stimulation and either innervated muscle twitch in the case of a motor nerve or altered sensation in a specific area in the case of a sensory nerve. Ultrasound is used to visualize the nerve and structures closely associated with the nerve (e.g. vessels) to assist in placing the cryoprobe in close proximity to the target nerve. By positioning the patient's skeletal structure in a predetermined position (e.g. knee bent 30 degrees or fully extended), one can reliably position the bones, ligaments, cartilage, muscle, soft tissues (including fascia), vasculature, and peripheral nerves. External palpation can then be used to locate the skeletal structure and thereby locate the pathway and relative depth of a peripheral nerve targeted for treatment.

A treatment of peripheral nerve tissue to at least −20° C. is sufficient to trigger 2nd degree Wallerian degeneration of the axon and mylinated sheath. Conduction along the nerve fibers is stopped immediately following treatment. This provides immediate feedback as to the location of the target peripheral nerve or associated branches when the associated motion or sensation is modified. This can be used to refine rigid landmark guidance of future treatments or to determine whether addition treatment is warranted.

By using rigid landmarks, one may be able to direct the treatment pattern to specific anatomical sites where the peripheral nerve is located with the highest likelihood. Feedback from the patient immediately after each treatment may verify the location of the target peripheral nerve and its associated branches. Thus, it should be understood that in some embodiments, the use of an electronic nerve stimulation device to discover nerve location is not needed or used, since well-developed treatment zones can locate target nerves. This may be advantageous, due the cost and complexity of electronic nerve stimulation devices, which are also not always readily available.

In alternative embodiments of the invention, one could use an electronic nerve stimulation device (either transcutaneous or percutaneous) to stimulate the target peripheral nerve and its branches. With transcutaneous electric nerve stimulation (TENS) the pathway of the nerve branch can be mapped in an X-Y coordinates coincident with the skin surface. The Z coordinate corresponding to depth normal to the skin surface can be inferred by the sensitivity setting of the electrical stimulation unit. For example, a setting of 3.25 mA and pulse duration of 0.1 ms may reliably stimulate the frontal branch of the temporal nerve when it is within 7 mm of the skin surface. If a higher current setting or longer pulse duration is required to stimulate the nerve, then the depth may be >7 mm. A percutaneous electrical nerve stimulator (PENS) can also be used to locate a target peripheral nerve. Based on rigid anatomical landmarks, a PENS needle can be introduced through the dermis and advanced into the soft tissues. Periodic stimulating pulses at a rate of 1-3 Hz may be used to stimulate nerves within a known distance from the PENS needle. When the target nerve is stimulated, the sensitivity of the PENS can be reduced (e.g. lowering the current setting or pulse duration) narrowing the range of stimulation. When the nerve is stimulated again, now within a smaller distance, the PENS sensitivity can be reduced further until the nerve stimulation distance is within the therapy zone dimensions. At this point, the PENS needle can be replaced with the focused cold therapy needle(s) and a treatment can be delivered. The PENS and focused cold therapy needles can be introduced by themselves or through a second larger gage needle or cannula. This may provide a rigid and reproducible path when introducing a needle and when replacing one needle instrument with another. A rigid pathway may guide the needle to the same location by preventing needle tip deflection, which could lead to a misplaced therapy and lack of efficacy.

While many of the examples disclosed herein related to puncturing the skin in a transverse manner to arrive at a target sensory nerve, other techniques can be used to guide a device to a target sensory nerve. For example, insertion of devices can be made parallel to the surface of the skin, such that the (blunted) tip of the device glides along a particular fascia to arrive at a target sensory nerve. Such techniques and devices are disclosed in U.S. Pub. No. 2012/0089211, the entirety of which is incorporated by reference. Possible advantages may include a single insertion site, and guidance of a blunt tip along a layer common with the path or depth of the target nerve. This technique may be a position-treatment—thaw, reposition treatment, thaw, etc.

While the exemplary embodiments have been described in some detail for clarity of understanding and by way of example, a number of modifications, changes, and adaptations may be implemented by persons of ordinary skill in the art after reading the disclosure provided herein. Hence, the scope of the present invention is limited solely by the claims as follows.

What is claimed is:

1. A system for treating a spasticity in a limb of a patient, the system comprising:

a cryogenic cooling needle having a proximal end, a distal end, and a lumen therebetween, the needle configured for insertion within a target tissue proximate to a motor nerve associated with the spasticity in the limb of the patient by bending the needle outside a body of the patient to access the nerve along a plane of the target tissue, wherein the needle has varying stiffness at a proximal portion and a distal portion, wherein the motor nerve is in the limb of the patient, wherein the needle comprises a cladding of conductive material conductively coupled to the proximal portion of the needle such that the proximal portion of the needle is configured to be stiffer than the distal portion of the needle, such that the distal portion deflects more easily than the proximal portion;

a cooling fluid supply lumen extending distally within the needle lumen to a distal portion of the needle lumen;

a cooling fluid source coupled to the cooling fluid supply lumen to direct cooling fluid flow into the needle lumen so that the cooling fluid vaporizes within the lumen to provide cooling to the motor nerve so as to treat spasticity;

a heater thermally coupled to a thermally responsive element and the proximal portion of the needle;

a first temperature sensor thermally coupled to the thermally responsive element;

a second temperature sensor thermally coupled to a different position on the thermally responsive element, wherein the second temperature sensor is closer to a tissue contacting surface of the needle than the first temperature sensor to provide a temperature differential between the first temperature sensor and the second temperature sensor; and a controller, wherein the controller is configured to receive temperature information of the thermally responsive element to determine an amount of power to provide to the heater to maintain the thermally responsive element at a predetermined temperature, wherein the controller is configured to initiate treatment in response to the temperature information being less than a threshold value, wherein the controller is configured to monitor power draw from the heater to characterize tissue type.

2. The system of claim 1, wherein the needle has a variable flexibility along its length and a different bending strength at the proximal portion and distal portion such that the proximal portion of the needle is more stiff than the distal portion of the needle so that the distal portion deflects more easily than the proximal portion.

3. The system of claim 1, wherein the needle is configured to resiliently bend at the distal portion by an angle up to 120 degrees.

4. The system of claim 1, wherein the nerve associated with the spasticity is in an upper limb of the patient.

5. The system of claim 1, wherein the cryogenic cooling needle comprises a length of greater than 7 mm.

6. The system of claim 1, wherein a treatment cycle is controlled by a processor, the treatment cycle based at least in part on a treatment instruction from an operator, the treatment cycle comprising at least one heating phase and at least one cooling phase, wherein the processor is configured to control the cooling fluid flow and the heater in response to operator input.

7. The system of claim 6, wherein the processor is further configured to provide an audio or visual alert to the operator.

8. The system of claim 7, wherein the audio or visual alert is an error flag activated in response to an out of normal condition.

9. The system of claim 8, wherein the out of normal condition comprises an indication of insufficient cooling.

10. The system of claim 6, wherein the processor is configured to control the cooling fluid flow and the heater in response to operator input.

11. The system of claim 10, wherein the processor is further configured to provide a degree of skin warming throughout the treatment cycle, wherein the degree of skin warming is between 28-42° C.

12. The system of claim 10, wherein the at least one heating phase comprises a pre-warm phase with the heater before the at least one cooling phase, wherein the pre-warm phase has a duration less than 12 seconds.

13. The system of claim 10, wherein during the at least one cooling phase the cryogenic cooling needle generates a cryozone having a volume of 65-105 $mm^3$.

14. The system of claim 10, wherein the at least one cooling phase has a duration of 5 seconds to 120 seconds.

15. The system of claim 10, wherein the processor is configured to provide an audio or visual alert at completion of the treatment cycle.

16. The system of claim 1, further comprising a supply valve for modulating a flow rate of the cooling fluid.

17. The system of claim 16, wherein the supply valve is actuated by a control signal from the controller.

18. The system of claim 1, further comprising:

a body comprising a handpiece having a size and shape suitable for supporting in a hand of an operator, the body supporting the needle, wherein the cooling fluid source is disposed in the handpiece.

19. A system for treating a spasticity in a limb of a patient, the system comprising:

a cryogenic cooling needle having a proximal end, a distal end, and a lumen therebetween, the needle configured for insertion within a target tissue proximate to a motor nerve associated with the spasticity in the limb of the patient by bending the needle outside a body of the patient to access the nerve along a plane of the target tissue, wherein the needle has varying stiffness at a proximal portion and a distal portion, wherein the motor nerve is in the limb of the patient, wherein the needle comprises a cladding of conductive material applied to an exterior surface of the proximal portion of the needle and conductively coupled to the proximal portion of the needle such that the proximal portion of the needle is configured to be stiffer than the distal portion of the needle, such that the distal portion deflects more easily than the proximal portion;

a cooling fluid supply lumen extending distally within the needle lumen to a distal portion of the needle lumen a needle probe coupling the proximal portion of the needle to the cooling fluid supply lumen, the needle probe further comprising a heater element and a conductive block coupled to the cladding, wherein the cladding extends from within the needle probe, the heater element, and the conductive block and along the proximal portion of the needle forming an exposed length of the cladding; and a cooling fluid source coupled to the cooling fluid supply lumen to direct cooling fluid flow into the needle lumen so that the cooling fluid vaporizes within the lumen to provide cooling to the motor nerve so as to treat spasticity; and a controller, wherein the controller is configured to monitor power draw from the heater element in order to perform device diagnostics and determine tissue conditions.

* * * * *